US006810382B1

(12) United States Patent
Wamsley et al.

(10) Patent No.: US 6,810,382 B1
(45) Date of Patent: Oct. 26, 2004

(54) PERSONAL INJURY CLAIM MANAGEMENT SYSTEM

(76) Inventors: Vaughn A. Wamsley, 6333 N. Washington Blvd., Indianapolis, IN (US) 46220; Brant Davidson, 1101 Basswood Cir., Bloomington, IN (US) 47403; David L. Cantwell, 1414 Monroe Dr., Carmel, IN (US) 46032

(*) Notice: Subject to any disclaimer, the term of this patent is extended or adjusted under 35 U.S.C. 154(b) by 0 days.

(21) Appl. No.: 09/303,199

(22) Filed: Apr. 30, 1999

Related U.S. Application Data

(63) Continuation of application No. 08/826,559, filed on Apr. 4, 1994, now Pat. No. 5,956,687.

(51) Int. Cl.[7] ............................................. G06F 19/00
(52) U.S. Cl. ......................................... 705/1; 707/530
(58) Field of Search ............................... 707/100, 101, 707/102, 530; 705/7, 8, 1, 2, 3, 4

(56) References Cited

U.S. PATENT DOCUMENTS

| | | | |
|---|---|---|---|
| 4,837,693 A | | 6/1989 | Schotz |
| 5,043,891 A | * | 8/1991 | Goldstein et al. ........... 707/530 |
| 5,175,681 A | | 12/1992 | Iwai et al. |
| 5,191,522 A | | 3/1993 | Bosco et al. |
| 5,241,466 A | | 8/1993 | Perry et al. |
| 5,267,155 A | | 11/1993 | Buchanan et al. |
| 5,329,447 A | | 7/1994 | Leedom, Jr. |
| 5,369,704 A | | 11/1994 | Bennett et al. |
| 5,392,428 A | * | 2/1995 | Robins ....................... 707/101 |
| 5,444,615 A | | 8/1995 | Bennett et al. |
| 5,815,392 A | * | 9/1998 | Bennett et al. ................. 705/8 |
| 5,838,966 A | * | 11/1998 | Harlan ....................... 707/100 |
| 5,875,431 A | * | 2/1999 | Heckman et al. .............. 705/7 |
| 5,940,800 A | * | 8/1999 | Bennett et al. ................. 705/8 |
| 5,956,687 A | | 9/1999 | Wamsley et al. .............. 705/1 |
| 5,991,733 A | * | 11/1999 | Aleia et al. .................... 705/8 |
| 6,128,620 A | * | 10/2000 | Pissanos et al. ............ 707/102 |

OTHER PUBLICATIONS

"Picking a Case Management Software System", by James A. Eidelman, published in Practical Litigator, Sep. 1992.*
*ST Software Technology, Inc. Product Information Packet*; Software Technology, Inc., Lincoln, Nebraska (date unknown).
*ST Software Technology, Inc.,Product Information on Internet Homepage*; Sep. 19, 1996, Software Technology, Inc., Lincoln, Nebraska.

(List continued on next page.)

*Primary Examiner*—Sam Rimell
(74) *Attorney, Agent, or Firm*—Woodard, Emhardt, Moriarty, McNett & Henry LLP

(57) ABSTRACT

A technique for computerized management of a plaintiff's personal injury case is disclosed. This technique includes establishing records, each reflective of the phase of a corresponding personal injury claim. The first phase corresponds to pre-negotiation of the claim and includes at least a first and second subordinate pre-negotiation stage. Each of these stages includes the generation of a number of prompts directed to obtaining information about the claim. A given record may also be set to a second management phase corresponding to negotiation of the claim or a third management phase representing settlement of the claim. In addition, the present invention discloses a technique to automatically generate a demand letter and calculate settlement amounts from information gathered in the record during pursuit of the claim. The management system may also include scheduling various prompts and correspondence with the program in accordance with a predetermined schedule spanning several days.

24 Claims, 22 Drawing Sheets

Microfiche Appendix Included
(58 Microfiche, 3411 Pages)

OTHER PUBLICATIONS

*Welcome to LAN–TECH, Product Information on Internet Homepage; Sep. 12, 1996, LAN–TECH, Inc., Marietta, Georgia.

*Jr. Partner Plus Product Information; Millennium Software, Ltd., Conshohocken, Pennsylvania (at least as early as Sep. 1996).

*dLegal System, Product Information on Internet Homepage; Sep. 17, 1996, dLegal System, Hermitage, Pennsylvania.

*Versys, Product Information on Internet Homepage; Sep. 17, 1996, sales@versys.com (e–mail address).

*Parallax Legal Software, product Information on Internet Homepage; Sep. 17, 1996, Parallax MicroSystems, Inc., Cleveland, Ohio.

*CasePro, Product Information on Internet Homepage; Sep. 17, 1996, PC Solutions, North Syracuse, New York.

*CasePro Software Promotional Materials; PC Solutions, North Syracuse, New York (date unknown).

*Abacus Law; Product Information on Internet Homepage; Sep. 17, 1996, Abacus Data Systems, Inc., San Diego, CA.

*Abacus Law+ Faxdemo; Abacus Data Systems, Inc., San Diego, CA; (Sep. 18, 1996).

*Abacus Software Promotional Letter; 1995, Abacus Data Systems, Inc., San Diego, CA.

*Abacus Software Brochure; 1992, Abacus Data Systems, Inc., San Diego, CA.

*Time Matters, Product Information on Internet Homepage; (at Least as Early as 1996), Data Txt Corporation.

*Tme Matters Brochure; Data.Txt Corporation (at least as early as 1996).

*Time Matters Promotional Bulletin; Dec./Jan., 1996, Data.Txt Corporation.

*Pins & Needles, Product Information Packet; Chesapeake Interlink, Ltd., Owings Mills, MD.

*Needles Software Information Bulletin #33; 1995, Chesapeake Interlink, Ltd., Owings Mills, MD.

*ST Software Technology, Inc., Case Master III; Software Technology, Inc., Lincoln, Nebraska (date unknown).

*ST Software Technology, Inc., Tabs III; Software Technology, Inc., Lincoln, Nebraska (date unknown).

*Needles software demonstration printout (date unknown).

*Needles Demo Disk #1; believed only to be available on electronic media.

*Needles Demo Disk #2; believed only to be available on electronic media.

*Needles Demo Disk #3; believed only to be available on electronic media.

*Case Master III Demo for Windows; believed only to be available on electronic media.

*STI Demo Disk Version 8; believed only to be available on electronic media.

Declaration of Vaughn A. Wamsley concerning events prior to Apr. 4, 1997.

* cited by examiner

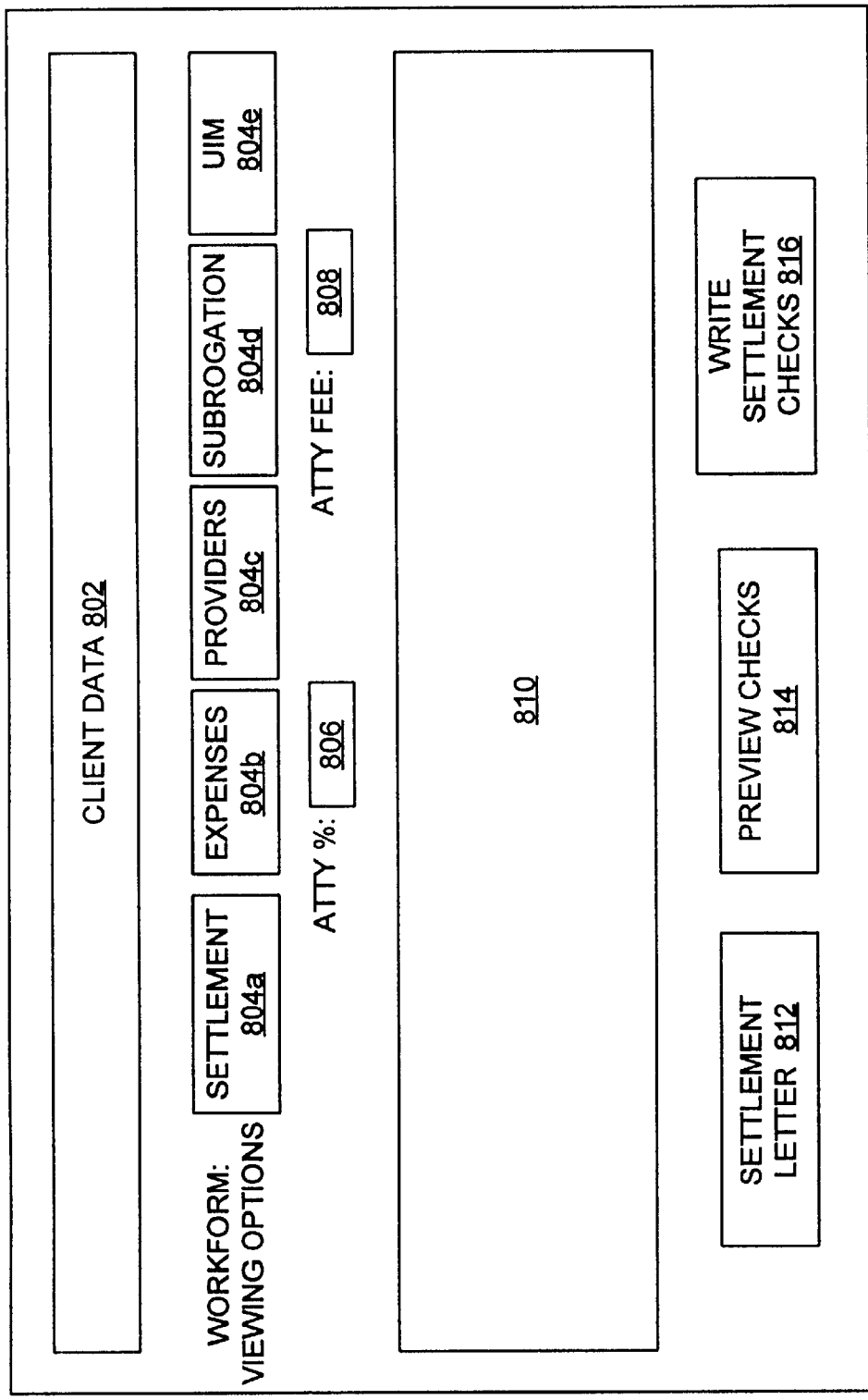

PERSONAL INJURY CLAIM MANAGEMENT SYSTEM

This application is a continuation of Ser. No. 08/826,559 filed Apr. 4, 1994 now U.S. Pat. No. 5,956,687.

MICROFICHE APPENDIX

A computer program listing is included herewith as a microfiche appendix with a total of 58 fiche sheets and 3,411 frames.

BACKGROUND OF THE INVENTION

The present invention relates to the computerized management of client data, and more particularly, but not exclusively relates to the management of personal injury claims.

Every year vast numbers of personal injuries occur. The law encourages injured parties to seek compensation from those at fault. Typically, the injured party, the plaintiff, is able to obtain compensation from the party at fault, the defendant (or the defendant's insurer), by threatening a lawsuit. In the vast majority of cases, the claim of the injured party is settled before a trail on the merits results—even before a lawsuit is filed in many cases. By settling legitimate claims quickly, a more cost-effective conclusion is reached for all parties involved. Moreover, early settlements conserve judicial resources to the benefit of the public at large.

Unfortunately, efficiently settling these claims ordinarily requires the coordination and scheduling of doctors, lawyers, insurance representatives, and many others. Generally, the pursuit of a personal injury claim also requires the injured client's legal representative to gather and assimilate large quantities of documents and other information from a variety of sources. Once gathered, this information is used to negotiate a settlement of a claim or litigate the claim as the situation warrants. Frequently, poor coordination, scheduling, and information management leads to claims that are not settled promptly, properly, or fairly. Sometimes, a poorly managed claim becomes the subject of costly litigation which otherwise could have been avoided.

In addition, information collection tasks often limit the quantity of claims that can be handled at the same time by a given number of legal support personnel. The management of information collection required for some claims often distracts legal representatives from focusing on negotiation and litigation tasks for other claims. This distraction significantly adds to cost and hampers efficiency of the typical personal injury attorney's practice.

Conventional management schemes are often prone to errors due to the imposition of a manual entry in a client's file every time a document is sent or other noteworthy event takes place. Moreover, these schemes do not prompt the legal representative or support staff to assure the prompt advancement of the claim from one stage to the next. The untimely advancement of a claim through various information gathering and evaluation stages often results in a more expensive and protracted resolution of the claim compared to claims which are investigated, evaluated, and asserted more promptly. Also, conventional schemes often make it difficult to quickly access the status of a given client's case in response to a phone call or other request requiring a quick turn around.

Consequently, there remains a need for a personal injury management technique to automatically gather, track, schedule, and organize various aspects of personal injury claims. Preferably, such a system facilitates a rapid assessment of the status of each claim, and frees legal representatives from tedious and burdensome information management tasks. Instead, legal representatives may focus on negotiation and litigation of meritorious claims—increasing the number of claims which may be handled simultaneously and improving quality of the representation. As compared to conventional schemes, it is preferred that this management technique facilitate the handling of a larger number of claims by the same legal support staff with fewer errors. Moreover, the system promotes movement of a number of personal injury claims towards settlement in a timely manner. The present invention meets these needs and provides other significant advantages.

SUMMARY OF THE INVENTION

The present invention relates to legal claim management. Various aspects of the invention are novel, non-obvious, and provide various advantages. While the actual nature of the invention covered herein can only be determined with reference to the claims appended hereto, certain features which are characteristic of the preferred embodiment disclosed herein can be described briefly.

In one feature of the present invention, a computerized management technique for a plaintiff's personal injury case includes executing a program loaded on a computer to establish a client data record. This record has data relative to a personal injury claim including status of the claim. Status of the record is established in a first management phase which corresponds to pre-negotiation of the claim. The program characterizes the first phase with at least a first subordinate pre-negotiation stage and a second subordinate pre-negotiation stage. The program generates a first number of pre-negotiation prompts in response to initiation of the first stage. These first prompts are directed to obtaining information about the claim. The second stage of the first phase is activated after completion of medical treatment of an injury corresponding to the claim. The program generates a second number of pre-negotiation prompts in response, which are directed to the determination of a proposed settlement amount for the claim. The status of the record is set to a second management phase corresponding to negotiation of the claim, and a third management phase representing settlement of the claim. This computerized management system provides a unique organizational structure that facilitates advancement of a personal injury claim through an optimal sequence of information gathering stages with a minimum of manual intervention.

In another feature, a computerized management system includes establishing a number of data records in a computer by executing a program. Each of the records corresponds to a different personal injury claim which is opened with a first status representing a medical treatment phase for a corresponding injury. The program prompts generation of a first number of documents in accordance with a first schedule timed by the program to span a first number of days for each of the records. The first documents are correspondingly directed to receiving information about the claim for each of the records. The first status of a selected one of the records is changed to a second status in accordance with completion of medical treatment for the corresponding injury. The program prompts generation of a second number of documents different from the first number of documents in accordance with a second schedule initiated by the status change. The program times the second schedule to span a second number of days. The second documents are directed to formulation of a proposed settlement amount for the injury. The selected one of the records is switched to a third status in response to communicating the proposed settlement amount to a corresponding opponent. The selected one of the records is set to a fourth status corresponding to litigation of the corresponding claim. The program prompts generation of a third number of documents in accordance with a third schedule timed by the program during the fourth status. Generation of selected ones of the first, second, and third documents may automatically update the corresponding record and trigger one or more prompts to follow-up on whether a response has been received to the document triggering the update.

In still another feature of the present invention, a computer system for managing a number of personal injury cases includes an input device, a video monitor, and a processor. The processor responds to the input device to generate a number of data records each corresponding to a different respective personal injury claim. The processor generates a number of signals for each of the records, which include a first control signal corresponding to pre-negotiation of the respective claim. The first control signal is characterized by at least two subordinate signals. These subordinate signals include a first subordinate signal corresponding to medical treatment of an injury associated with the respective claim. The processor is responsive to the first subordinate signal to time generation of a first number of prompt signals in accordance with a first schedule spanning several days. These subordinate signals also include a second subordinate signal corresponding to release from medical treatment for the injury. The processor is responsive to the second subordinate signal to time generation of a second number of prompt signals in accordance with a second schedule spanning several days. The second prompt signals differ from the first prompt signals. The number of signals generated by the processor also include a second control signal corresponding to negotiation of the respective claim and a third control signal corresponding to settlement of the respective claim. The monitor responds to the first prompt signal to display a first number of input prompts in accordance with the first schedule and to the second prompt signals to display a second number of input prompts in accordance with the second schedule. The first and second prompts facilitate gathering and entry of data about the respective claim into a corresponding one of the records.

In still another feature of the present invention, a device for a computer system having a processor, video monitor, and printer is provided which includes a computer readable medium storing a software program. The program generates a number of data records each corresponding to a different respective personal injury claim. The program places each of the records in a first management phase corresponding to pre-negotiation of the respective claim. The program characterizes the first phase with at least a first subordinate stage corresponding to medical treatment for an injury associated with the respective claim and a second subordinate stage corresponding to completion of medical treatment for the injury. The program displays a number of prompts on the monitor in accordance with a first schedule spanning a first number of days and generates a second number of corresponding documents with the printer during the first stage. The program times display of a second number of prompts on the monitor in accordance with the second schedule spanning a second number of days and generates a second number of corresponding documents with the printer during the second stage. The program is configured to selectively classify the records in a second management phase corresponding to negotiation of the respective claim and a third management phase corresponding to settlement of the respective claim.

In yet another feature, a computerized management technique includes establishing a number of data records in a computer system for processing by a software program executed by the system. The records each correspond to one of a number of personal injury claims. The claims each correspond to a respective client suffering a respective personal injury. A number of data items are entered into each of the records. The items include a factual description of the respective injury, a number of values corresponding to damages suffered by the respective client, and an address of an opponent to a corresponding claim. One of the records is selected to generate a demand letter with the system. The program automatically assembles the letter from a standard form, the items corresponding to the selected record, and a demand amount calculated by the program from the values corresponding to the selected one of the records.

In a further feature of the present invention, a number of data records are established in a computer by executing a program, which each correspond to a different personal injury claim. Each record is opened with a first management phase representing medical treatment for a corresponding injury. A selected one of the records is changed from the first phase to a second management phase in accordance with completion of medical treatment for the corresponding injury. This record is switched to a third management phase in response to communication of the proposed settlement amount to a corresponding opponent. The status of the selected one of the records is changed to a fourth management phase representing settlement of the corresponding personal injury for a final settlement amount. The program calculates a distribution of the final settlement amount among a number of recipients and prompts generation of a corresponding number of checks with the computer. The selected one of the records includes a number of accounting entries. A first one of the entries corresponds to a medical cost for the corresponding injury, and a second one of the entries corresponds to an expense incurred during the second or third phases to pursue the corresponding claim. The distribution is calculated by the program as a function of the entries.

Accordingly, it is one object of the present invention to provide a technique for computerized management of personal injury claims.

Another object is to provide a computerized multi-phase management system having subordinate stages for at least one of the phases.

Another object of the present invention is to provide a technique for advancing a personal injury claim through various information gathering and evaluation stages to prompt a timely settlement.

A further object is to provide a computerized personal injury claim management technique which facilitates the prompt assessment of the status of a claim selected from a large number of claims.

Yet another object is to provide a computerized management system which generates a letter by automatically assembling data from a client record and calculating relevant quantities for inclusion in the letter.

Another object is to assist legal support staff in the timely and efficient gathering of information from which to formulate a settlement proposal.

A further object is to reduce errors inherent in conventional systems which require manual entry of the dates documents are sent.

It is still another object of the present invention to provide a computerized management technique for generating demand letters and settlement amounts to facilitate efficient personal injury claim management.

Further objects, advantages, benefits, aspects, and features of the present invention will become apparent from the description and drawings contained herein.

BRIEF DESCRIPTION OF THE DRAWINGS

FIG. 9 is a diagram depicting a user interface for the computerized determination of settlement disbursements of personal injury claims.

DESCRIPTION OF THE PREFERRED EMBODIMENT

Figure 1:
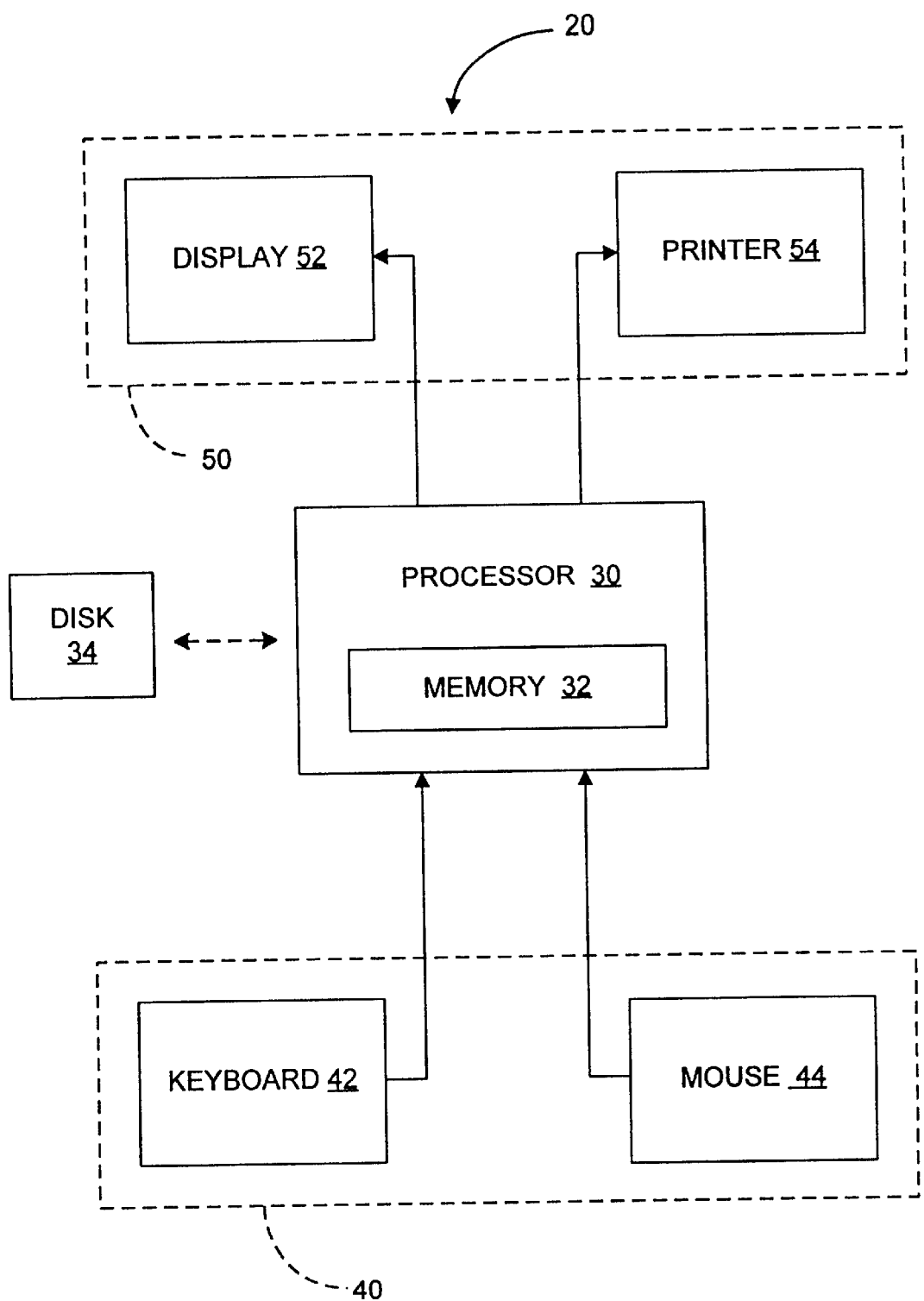
FIG. 1 is a schematic view of a hardware system.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates.

FIG. 1 is a schematic view of computerized processing system 20 of one embodiment of the present invention. System 20 includes processor 30 operatively coupled to input devices 40 and output devices 50. Processor 30 is configured to perform one or more predetermined routines to process information residing in memory 32. In one preferred embodiment, system 20 is configured to execute management program software corresponding to the computer program listing of the Microfiche Appendix.

Processor 30 is also configured to receive portable disk 34 for remotely storing computer readable information. Input devices 40 include keyboard 42 and mouse 44. Devices 40 are used to provide operator input to processor 30 as required. Output devices 50 include visual display 52 and printer 54. Devices 50 are used to provide output from routines executed by processor 30 in response to input from devices 40. System 20 may further include other input or output devices such as a modem, network link, speaker, microphone, or such other devices as would occur to one skilled in the art.

Processor 30 may be a collection of one or more electronic components or a single custom integrated component. Processor 30 may include digital circuitry, analog circuitry, or a combination of these circuit types. Although it is preferred that the processor be readily reprogrammable by software, it may also be programmed by firmware, configured as a integrated state machine, or employ a combination of these techniques. Preferably, processor 30 is configured to digitally receive, process, and output information in a conventional manner; however, it is envisioned that the present invention may be adapted to other types of processing techniques as would occur to those skilled in the art.

Preferably, memory 32 is of the electronic (e.g. solid state), magnetic, or optical variety which may be readily interfaced with electronic controllers or processors. Memory 32 may be integrally associated with system 20 or be remotely accessed via a communication link with system 20. Disk 34 participates in system 20 as an optionally available memory accessible by processor 30. Disk 34 may be a removable optical disk (CD), electromagnetic Hard or floppy disk media, or other portable memory type as would occur to one skilled in the art. Display 52 is preferably of the color graphic Cathode Ray Tube (CRT) variety. Alternatively, a liquid crystal display or other visual display responsive to processor 30 may be used. Printer 54 is preferably of the laser variety, but could be of another type as would occur to one skilled in the art.

It is preferred that system 20 be a conventional desktop microprocessor-based personal computer system. In one embodiment, processor 30 includes a base unit with a PENTIUM microprocessor supplied by INTEL corporation configured to operate at a 200 MHz clock speed. The base unit also includes memory 32 comprising 32 megabytes (MB) of conventional semi-conductor Random Access Memory (RAM) components and at least one conventional electromagnetic hard disk drive unit compatible with the microprocessor. Also, it is preferred that the base unit include a conventional floppy disk drive configured to receive a 1.44 MB electromagnetic floppy disk as disk 34. For this embodiment, keyboard 34 and mouse 44 are of a conventional variety compatible with the base unit and operatively connected thereto by appropriate cables. Similarly, display 52 is provided by a VGA monitor cabled to the base unit with at least an 800×600 pixel resolution, and printer 54 is of a compatible laser variety cabled to the base unit. System 20 includes all the electrical and electronic components needed to provide a functional, personal desktop computer for this embodiment. This 200 MHz PENTIUM-based personal computer embodiment of system 20 is preferred for the execution of the computer program listing of the Microfiche Appendix.

Figure 2:
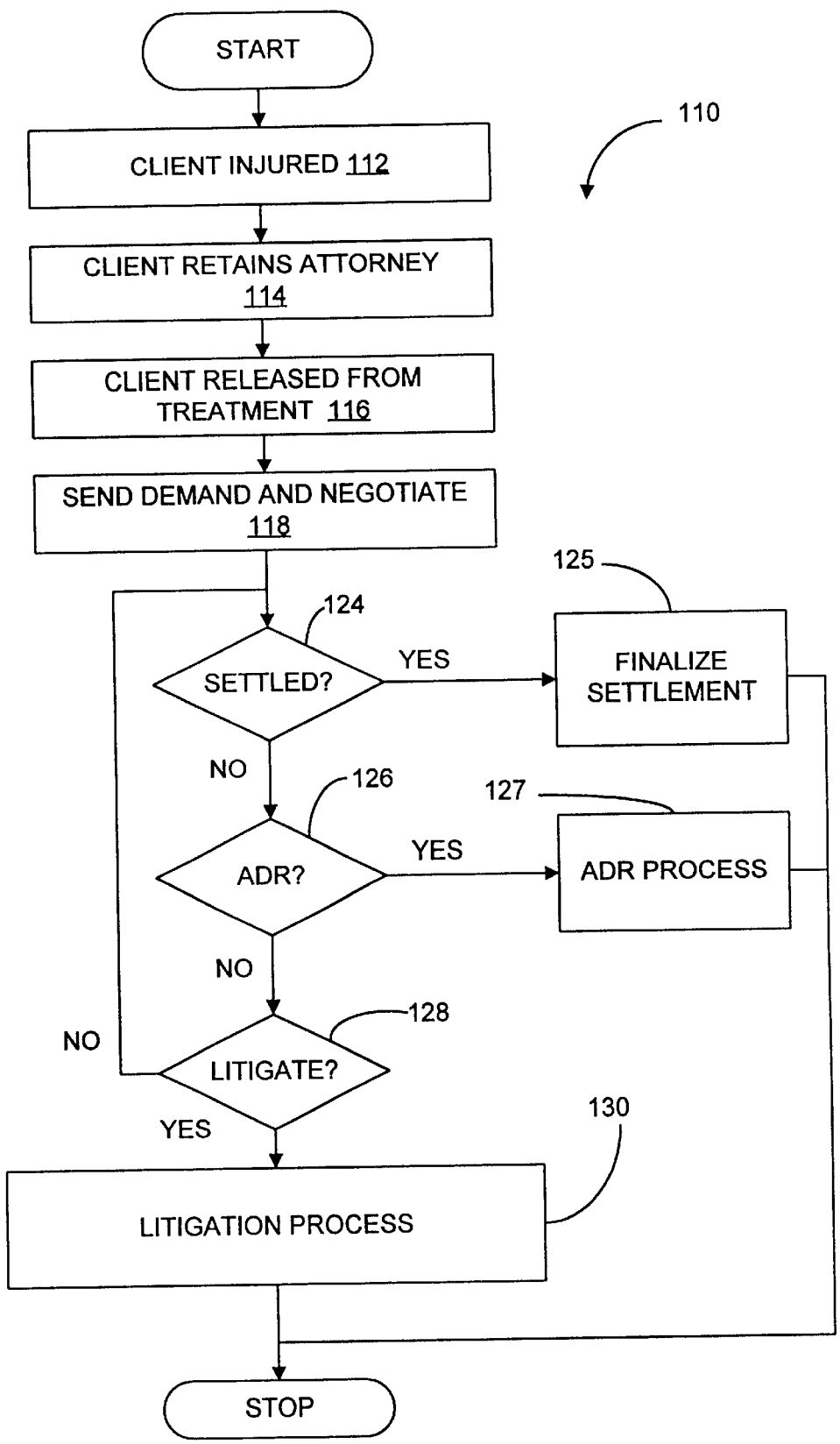
FIG. 2 is a flow diagram of a personal injury claim process.

FIG. 2 is a flow chart illustrating personal injury claim process 110. Process 110 begins with stage 112. In stage 112, a client is injured and contacts an attorney to have their personal injury claim evaluated. If the client decides to retain the attorney and the attorney accepts the case, control flows to stage 114, otherwise the process terminates (not shown in FIG. 2). Stage 114 includes initiation of a computer client data record with a management program executed by system 20, a preferred embodiment of this management program is listed in the Microfiche Appendix. Preferably, the management program supports a large number of independently accessible client data records. Information available at stage 114 is entered into the client's data record via one or more of input devices 40. Stage 114 corresponds to a time period during which the client is receiving medical treatment for the injury. Because the extent and cost of the injury is not yet known, negotiation of the client's claim with the party that caused the injury generally does not commence during stage 114. However, information concerning the event that caused the injury, such as a slip and fall or an automobile accident, may be gathered. Also, the attorney preferably checks on the treatment progress of the client and educates the client as to the personal injury claim process.

Upon release of the client from medical treatment, stage 116 is initiated. Although some information concerning the scope and nature of the personal injury claim is gathered during stages 112 and 114, stage 116 focuses on obtaining information specific to establishing a fair compensation amount for the client. For example, medical provider records and bills, and information concerning economic loss, such as lost wages, are gathered in stage 116. Once the appropriate information is gathered, it is presented in a persuasive letter to the person who caused the injury (the defendant), the defendant's representative, or the defendant's insurance company. This "demand letter" proposes an amount of compensation needed to settle the client's claim, initiating a negotiation phase of the case. In contrast, stages 112, 114, and 116 correspond to a pre-negotiation period of the client's claim. Notably, stage 116 is still a part of pre-negotiation, but is also given the more specific designation of "Demand in Progress."

After the demand letter is sent, stage 118 is entered. During stage 118, negotiations between representatives of the client (or plaintiff) and defendant take place. Frequently, the claim is settled during this negotiation period. The prompt and proper execution of stages 114 and 116 during pre-negotiation enhance the chances that a settlement will be obtained promptly. However, on occasion, litigation or an Alternative Dispute Resolution (ADR) procedure is initiated. The decision to settle or engage one of the alternative procedures are represented by loop 120. In loop 120, conditional 124 tests whether the claim has been settled. If no settlement has occurred, then conditional 126 is encountered which tests whether and ADR procedure has been put in place. If there is no ADR procedure in place, then control flows to conditional 128 which tests whether litigation has been initiated. If litigation has not been initiated, control flows back to conditional 124 via loop 120 until one of the series of conditionals 124, 126, 128 is satisfied. The execution of loop 120 may generally be regarded as a occurring simultaneously with the negotiation phase of the client's claim.

If conditional 124 is satisfied, then control flows to stage 125 to finalize settlement. Settlement represents a final phase of the client's claim. Stage 125 includes receipt of a check in the amount of the settlement, payment of all parties owed on behalf of the client, and the execution of settlement papers. Quite often, an attorney representing a personal injury client pays various expenses incurred in pursuit of the client's claim out-of-pocket, relying on settlement proceeds to be repaid. Typically, the attorney's fee is paid as a percentage of the compensation proceeds which result only when the case is settled or a favorable ADR or litigation outcome is obtained. In addition, medical providers may be paid from settlement proceeds. Also, another party may be entitled to a portion of the proceeds by way of subrogation or a lien. The accounting and tracking of these payments presents a substantial challenge which is met by the present invention as described in connection with FIG. 9 hereinafter.

If conditional 126 of loop 120 is satisfied, then either a mediation or arbitration hearing is conducted in stage 127. Unlike a court proceeding, ADR procedures are typically privately funded and privately conducted. Ordinarily, a statement is filed with the mediator or arbitrator, but the exhaustive discovery and briefings associated with litigation are usually avoided. Stage 127 assumes termination of the process with the ADR procedure; however, in other embodiments, litigation or settlement stages may be encountered after stage 127 (not shown). ADR may be considered a separate phase of the claim or alternatively as a part of the negotiation or litigation phase.

If conditional 128 is satisfied, then litigation stage 130 is encountered. The litigation phase of a claim may include the operation of many concurrent procedures which generally increase the cost of pursuing the claim. Stage 130 is initiated by filing a formal document with the court called a "complaint." The clerk of the court stamps a copy of the complaint with the filing date and returns it to the attorney who filed it. The parties being sued are formally notified of the litigation by service of the complaint. Frequently, an informal notice is sent via letter by the attorney representing the injured client as well. The party or parties being sued formally respond to the complaint by filing a document with the court called an "answer" within a specified time period. Usually, this time period may be extended by filing a motion to enlarge the time required to answer.

Generally, personal injury claimants are required to file a "complaint" within a set time period imposed by a statute of limitations or their claim cannot be enforced. This time period is typically measured from the date of injury. Thus, when an amount of time has lapsed which is close to the statute of limitations, it may be necessary to promptly file a complaint just to preserve the client's rights. This procedure is not reflected in FIG. 2.

Another litigation procedure which may be initiated upon filing the complaint is discovery. Generally, discovery is a process employed by a party of the lawsuit to obtain information about the case from another party. Typically, informal or "paper" discovery comprises written interrogatories, which ordinarily require the opponent to provide a written response, and requests for production of documents and things that are expected to lead to relevant evidence. In contrast, formal discovery includes interrogating witnesses under oath in accordance with a procedure resembling the examination of a witness in court.

This interrogation of a witness through discovery is called a "deposition" which is usually held in the presence of a qualified court reporter who generates a transcript of the proceeding. A deposition may be imposed on any party to the lawsuit and on third party witnesses under certain circumstances. These discovery techniques are typically utilized a number of times before trial. Various court rules control the scope of discovery and impose time limits on the time to respond to each item. Often, response times for informal discovery may be extended when the court grants a motion filed by one of the parties for an enlargement of time to respond.

As trial nears, other litigation procedures tend to dominate. Often, dispositive motions, such as summary judgment motions, are filed. A summary judgment motion asks the judge to decide an issue of the case as a matter of law; thus eliminating the need to conduct a trial as to that issue. Sometimes the entire case may be disposed of by summary judgment. A pre-trial conference is usually conducted by the court to make a final attempt at settlement and establish parameters for trial often including the trial date. Prior to trial, the injured client's attorney needs to verify that all required evidence and witnesses are available for trial. Preliminary and final witness and evidence lists are ordinary filed with the court. Also, "motions in limine" are filed to tentatively prevent the presentation of certain evidence during trial. Finally, the trial is conducted and the outcome reached.

Stage 130 assumes litigation through trial; however, it should be understood that many variations are possible. Quite often, settlement is reached during litigation which effectively concludes process 110 with stage 125 (although approval by the court may be additionally required). Similarly, an ADR procedure may be ordered by the court in the midst of stage 130. Many other variations are also possible.

Having outlined the personal injury claim process, various aspects of a software program configured to manage process 110 are next described. The computer program listing of the Microfiche Appendix is one embodiment of this program. A software program corresponding to this listing is configured for execution as an application of Microsoft Corporation's ACCESS 2.0 program. Software corresponding to the Microfiche Appendix computer program listing is executed by opening "PITS2.MDB" from the ACCESS 2.0 "File" menu. The Microfiche Appendix organizes the program listing into sections according to type, using ACCESS 2.0 terminology as follows: (1) Database, (2) Tables, (3) Queries, (4) Reports, (5) Macros, (6) Modules, and (7) Forms. Preferably ACCESS 2.0 is operating under a WINDOWS 3.1 user interface environment with a compatible Disk Operating System (DOS). Full functionality also requires the availability of WORD 6.0 and the existence of the directory "C:\PITS\DOCS" as may be conventionally established under DOS. The WORD 6.0, and WINDOWS 3.1 program are also supplied by Microsoft Corporation. In other embodiments, the program listing may be complied to operate as a stand-alone executable file or otherwise modified for execution in another operating environment using techniques known to those skilled in the art. In addition, functional features of this program listing may be used separately or otherwise modified as would occur to one skilled in the art without departing from the spirit of the present invention.

Figure 2A:
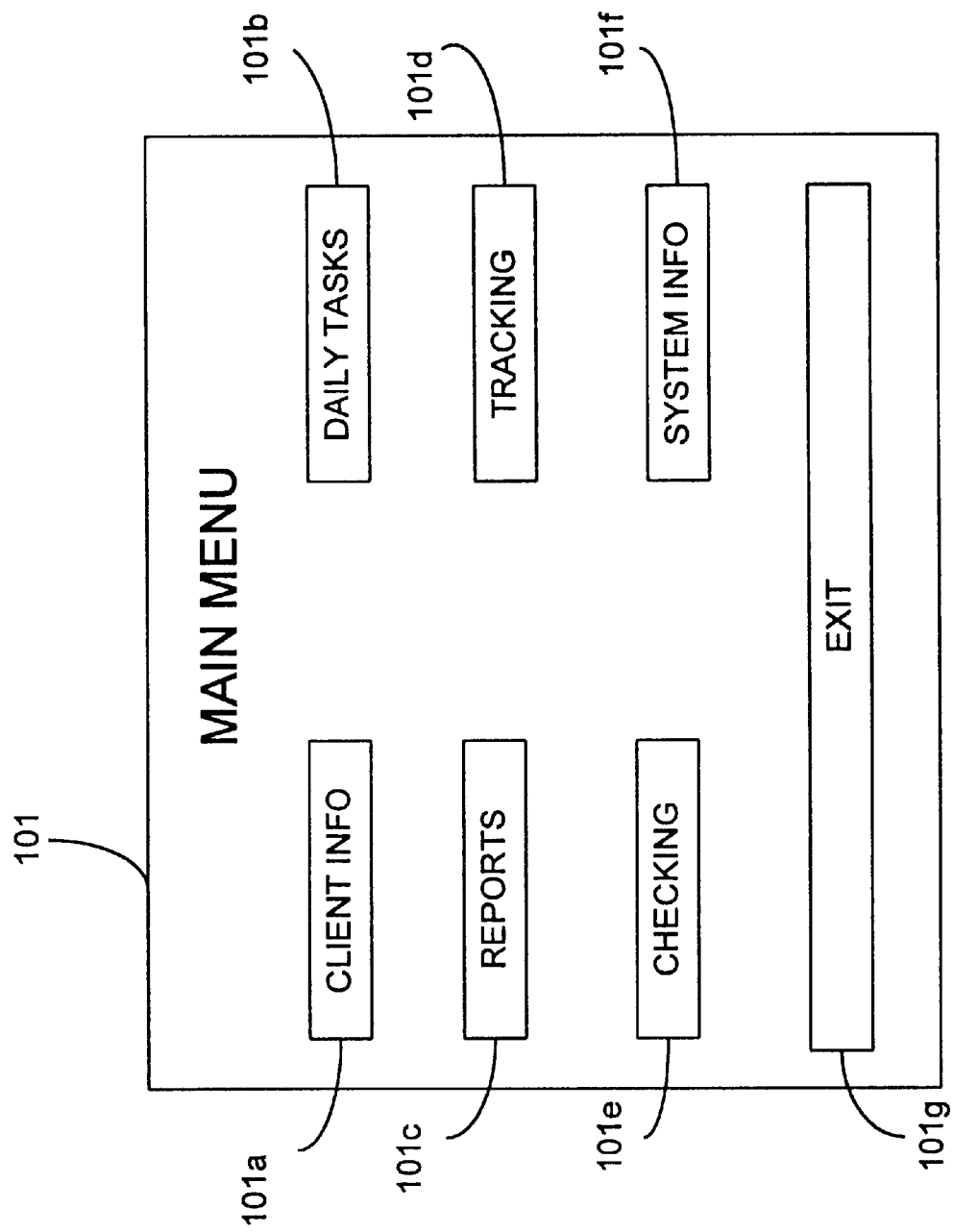
FIGS. 2A–2D are diagrams graphically depicting selected aspects of a user interface of a computer program to manage the process depicted in FIG. 2.
Figure 2B:
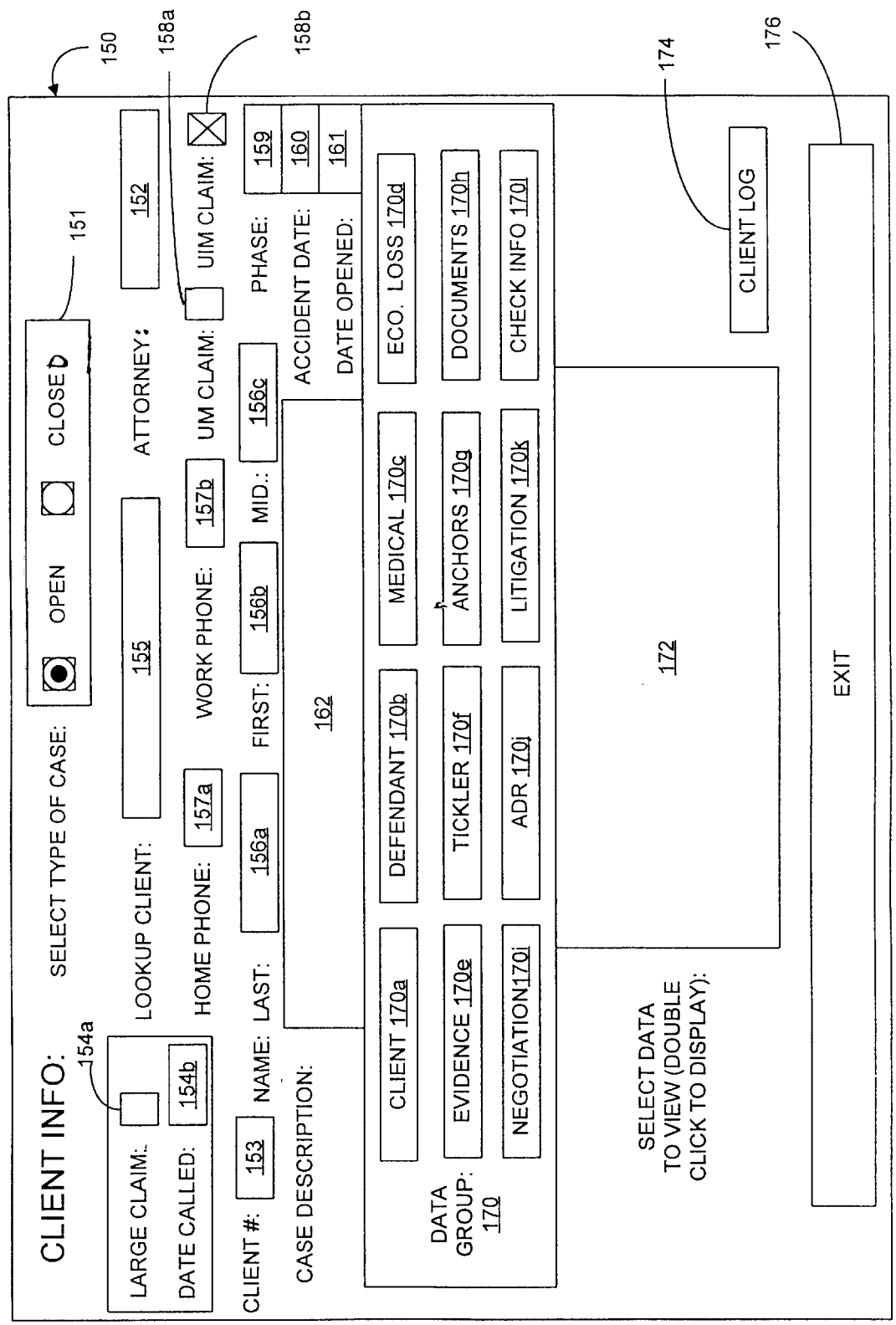

FIGS. 2A–2D illustrate selected user interfaces corresponding to the management program of the Microfiche Appendix. FIGS. 2A–2D each correspond to a graphical display generated by the management program and presented on display 52 for perusal by an operator. FIG. 2A illustrates an introductory display as main menu 101. Menu 101 includes button icon 101a which may be selected to generate Client Info form 150 as depicted in FIG. 2B. As used herein, a "button icon" is a graphical interface tool that may be selected or "activated" by a point and click operation with mouse 44 to correspondingly direct a desired operation of the management program.

Referring to FIG. 2B, Client Info form 150 displays selected data fields of a client data record. For a given record, one or more data fields may include information previously entered or be blank. Typically, the occupied data fields vary from record to record. Client records may be sequentially displayed and selected using pull-down menus and various button icons as are conventionally employed in the ACCESS 2.0 application environment. When a new record is added, the displayed data fields are typically blank and may be filled as required with keyboard 42 or mouse 44.

Generally, the management program is configured to support a number of client data records which each correspond to a different personal injury claim. As used herein, a "record" includes any group of information or data that may be indexed by one or more data fields or a collection of data field sets having one or more data fields in common. Data is entered into the various fields of each record with input devices 40 of system 20 and inserted through various operations of the management program. Operation 151 corresponds to a data field of the client record which is used to choose between open and closed client data records. Closed records correspond to client cases which have been settled or which are otherwise no longer active. Open records correspond to claims which are currently being pursued. The OPEN or CLOSED radio button icon of form 150 may be selected through a conventional point and click operation with mouse 44 to limit the display of client records to the corresponding type. In FIG. 2B, the OPEN selection is indicated.

Display block 152 corresponds to an attorney identity field which indicates the attorney assigned to the client's case. Radio button icons and check box icons may also correspond to data fields of the client record. For example, check box icon 154a corresponds to a Large claim field defined by the client record. Box icon 154a is marked through a standard point and click operation with mouse 44 when the claim resulted from a serious injury corresponding to a high compensation amount. The threshold for marking this box icon may vary as would occur to one skilled in the art. Display block 154b corresponds to a date data field which indicates when the attorney last called clients with the large claim status.

Display block 153 corresponds to a field of the client record containing a client number assigned by a program. Menu block 155 provides a pull-down menu of all clients for the selected type by pointing and clicking on block 155 with mouse 44. Preferably, the names of the clients are presented in alphabetical order in a scrollable, pull-down window when selected. Rapid movement through the window may be facilitated by typing a portion of the last name of the client being sought, once this pull-down menu is activated. After a desired name have been selected to reside at the top of the list, a point and click operation outside menu block 155 switches to the record for the selected client.

Display blocks 156a, 156b, 156c correspond to fields having the last, first, and middle name of the selected client, respectively. Display blocks 157a, 157b correspond to client record data fields having the home and work telephone number of the selected client, respectively. Check box icons 158a, 158b correspond to fields indicating the selected client has Uninsured Motorist (UM) and UnderInsured Motorist (UIM) protection. With this kind of protection, it is possible the client may be able to settle at least a portion of his or her claim from their own insurance company.

Display block 159 corresponds to a coded data field reflecting the status of the client's claim. The various status options are described briefly in table I as follows:

TABLE I

| Code | Description |
| --- | --- |
| PN | Pre-Negotiation phase of the client's claim; |
| DIP | Demand In Progress phase for the client's claim; |
| N | Negotiation phase of the clients claim; |
| L | Litigation phase of the client's claim; |
| S | Settlement phase of the client's claim; |
| D | Declined representation; and |
| Z | Record Closed. |

Display block 160 corresponds to a date field of the client record containing the date the client's accident or injury occurred. Display block 161 corresponds to a date field containing the date the client record is opened. Display block 162 corresponds to a text field of the client record in which a textual description of the client's case may be entered.

Button icon 174 is selected to view a client activity log. This log is automatically generated by the management program for each client record, and may be viewed as a report document and printed with printer 54. The management program automatically inserts at least a portion of the information contained in this log and inserts information entered into the client record throughout the pursuit of the client's claim. In effect, this log is structured to provide a hard copy of the information in the client's record as it existed at the time of selection. This log also facilitates direct manual entries as discussed hereinafter. Button icon 176 is selected to exit form 150.

Data group collection 170 includes an array of data group selection button icons 170a–170l. When one of button icons 170a–170l is selected, one or more data groups of the client record are listed in window 172. These groups may in turn comprise a number of data fields organized as one or more selectable records which are not displayed in form 150 due to space constraints. The data fields and subordinate records are typically linked by several common data fields such as the client name and the client number fields. The operator may branch to a form displaying the data of one of the groups through a mouse point and double click operation on the corresponding group name displayed in window 172.

When button icon 170a is selected, window 172 displays the data groups entitled: (1) Client Information, (2) Client Insurance, (3) Client Log Entry, (4) Subrogation, and (5) Workform. Selecting the Client Information group presents another display form, a client personal information form, which includes additional information about the client. This additional information corresponds to fields in the client data record which are not displayed in form 150. For example, this additional information may include the client's address, gender, social security number, and date of birth. The client personal information form also may include the attorney fee arrangement and a text field for miscellaneous notes concerning the client. Also, this form preferably provides a check box icon to track whether a medical treatment inventory letter has been sent to the client. Notably, the management program automatically marks this check box icon when an operator selects to generate the letter from the documents preparation routine of the management program. Another check box icon is included in the client personal information form to indicate whether a response to the medical inventory letter has been received. Also, a pulldown menu to select a police department from which to request a police report in the case of an automobile accident is provided in the client personal information form.

The client personal information form includes data fields for key dates such as the date of the accident, the date the client retains the attorney, and the date of settlement. The client personal information form presents fields also presented in the form 150 such as the client's name, case phase, and phone numbers.

If the Client Insurance group is selected, then a corresponding client insurance form is presented. This form provides the name, phone, and address of the client's insurer and describes selected coverage details. These details may include the amount of medical coverage, and the amount of any Uninsured motorist (UM) or Underinsured Motorist (UIM) coverage available. Also, the client insurance form includes a selection field to indicate acknowledgement of representation by the insurance company, and preferably includes a check box icon to flag whether the insurance coverage of the client's claim is questionable in some manner.

If the Client Log Entry group is selected, then a client log entry form is presented which allows the operator to manually enter items, notes, and reminders in the client activity log. The manual log entries are each maintained as a "sub-records" of the client data record. The client log entry form permits optional manual entries to be made in addition to entries automatically provided by various operations of the management program.

If the Subrogation group is selected, then a corresponding subrogation/lien form is displayed. This form displays one or more sets of information which each correspond to a party to which a payment is owed from the client's settlement by way of subrogation or a lien. The amount owed is also displayed for each of the parties indicated. Preferably, the subrogation/lien entries are indexed by client.

If the Workform group is selected, then a corresponding workform is displayed which is arranged to track monetary matters concerning settlement of the client's claim. One embodiment of this workform is depicted in FIG. 9 which is described hereinafter.

Button icon 170b of data group 170 is selected to display a data group list in window 172 including: (1) Defendant's Personal Information, (2) Defendant's Insurance Information, (3) Defendant's Independent Adjuster Information, (4) Defendant's Counsel Information, and (5) Defendant's "Mail To" Information. When the Defendant's Personal Information group is selected, a corresponding form is generated which displays the defendant's name and address. The defendant's personal information form also provides check box icon selections to indicate questionable liability or insurance, and acknowledge whether the defendant is represented by an insurer. In addition, date fields are displayed to indicate when a notice of representation letter was sent to either the defendant or defendant's insurance in accordance with an acknowledgement field, and when a response was received. A general note field is also included.

When the Defendant's Insurance Information group is selected, a corresponding form is displayed which presents the defendant's insurer, if any, with address and selected coverage details. When the Defendant's Independent Adjuster Information group is selected, a corresponding form is displayed which provides the name and address of the adjuster with other information as appropriate. Selection of the Defendant's Counsel Information group displays a form with the name and address of defendant's counsel (if any). Selection of the Defendant's "Mail To" Information indicates the address to which correspondence regarding the client's claim is to be sent.

When button icon 170c is selected, the following data groups are listed in window 172: (1) Provider List, (2) Provider Records, and (3) Provider Payment. When selected, the Provider List group presents a form configured to sequentially display each medical provider for the client. The form displays the medical providers name and address, the dates of medical treatment, and the nature of the medical treatment from corresponding fields of the client record. The Provider List form also permits access to a master list of health care providers to assist with entry of a new provider for the client.

Selection of the Provider Records group displays a form that is configured to sequentially display the status of medical records, medical treatment narratives, and treatment costs indexed by medical provider. The medical records form includes check box icons indicating which records are needed, whether a detailed narrative of the injury/treatment is needed, and the status of responses to requests for these items. The management program automatically updates the request status in the client data record when a medical record request is sent with the program. This update is preferably reflected in the client activity log and other selected reports generated by the management program. In addition, this form displays the date request letters were sent and the date of a follow-up phone call.

When the Provider Payment group is selected, a form is generated which is indexed by medical provider and client. The provider payment form is configured to sequentially display the payment status for each provider of the provider list, and includes check box icons to indicate whether a corresponding medical provider bill is needed or has been received. Also, the cost of treatment and the amount paid are indicated as appropriate. A verification check box icon is included to confirm when payment has been made.

When button icon 170*d* is selected, window 172 displays data groups relating to the client's economic loss resulting from the personal injury. The economic loss groups include: (1) an employer list and (2) employer records. Selection of the Employer List group provides a form to sequentially display the client's employers and corresponding addresses indexed by client. The Employer Records collection tracks requests and receipt of records relating to economic loss suffered by the client. When selected, an employer record form is displayed for each employer record entered. The employer record form includes two sets of data corresponding to lost wages records and loss of opportunity records, respectively. For each set, letter request dates and a follow-up telephone call date are displayed. The letter request fields are updated automatically when the management program is used to generate corresponding request letters. Also, is the amount of loss is displayed for each set.

Button icon 170*e* corresponds to data groups concerning evidence items for the client's case. The evidence groups include: (1) Evidence List and (2) Witnesses which are displayed in window 172 when button icon 170*e* is selected. Selection of the Evidence List group displays a form configured to sequentially display descriptions of various evidence items such as pictures of the injury causing accident, employment contracts, pay stubs, and the like. These items are indexed by client. Also, check box icons are provided to indicate request and receipt status of the evidence items. A check box icon is also provided to indicate receipt of a police report. Access to a master list of evidence descriptors may also be obtained from this form via a point and click button. Selection of the Witnesses group displays a form configured to sequentially present the name and address of each witness. In addition, check box icons are provided to indicate whether witness statements and questionnaires have been requested or received. The request field is entered automatically upon generation of a corresponding request letter with the management program. A check box icon is also provided to indicate if the witness is needed for trial.

Button icon 170*f* corresponds to date driven reminders or "ticklers" generated by a program. Generally, these ticklers are text reminders inserted into appropriate reports and worksheets and selectively presented with display 52. Ticklers prompt the operator to take a designated action on a predetermined date. The Tickler Data groups are presented in window 172 as: (1) view client daily ticklers and (2) set/view manual tickler items. Throughout the program, several types of ticklers may be employed. One type, an automatic tickler, is automatically scheduled in response to a designated event or other action. Automatic ticklers are often set by delivery of a request letter to prompt an automatic follow-up on the request a predetermined number of days after delivery. Once the request is satisfied, a corresponding entry is made in the client's record and the automated tickler is marked as completed by the management program so it is no longer generated. Indeed, document generation with the management program may generate a sequence of follow-up ticklers which are executed in accordance with a predetermined schedule until a response or other condition is satisfied. These types of ticklers are further discussed in connection with FIGS. 3–8.

Another type of tickler is manually set by the operator under the set/view manual ticklers form. Regardless of the origin of the tickler, selection of the view client daily tickler group results in a form that sequentially displays outstanding ticklers in relation to a specified date. The source of the tickler is indicated and a check box icon is also included which indicates whether the tickler has been completed. The view client daily ticklers form also provides various button icons to prompt action to satisfy the tickler (a "do it" command) which is typically used to assemble a pertinent letter or document with the management program for output with printer 54. Also, button icons are included to bring-up the client activity log and view/print various form documents.

Selection of the "set/view manual tickler items" data group provides a form to set and display manual ticklers for the selected client record. The data fields specified are the date the tickler is to be activated and the text reminder to be displayed on the activation date. Also provided is a "view tickler items" button icon which presents a report that may be previewed or printed. This tickler report displays the ticklers grouped according to whether open or completed. Within each group, the ticklers are listed chronologically.

Selection of button icon 170*g* displays "set/view client anchors" in window 172. To facilitate the timely and efficient gathering of information for a client's claim, a program is configured to track and gather client record information in accordance with a number of date-driven milestones or "anchors." Each anchor is activated by associating a start date or "anchor date" therewith. Once activated, each anchor triggers the generation of a sequence of ticklers or other prompts in accordance with a predefined schedule measured relative to the anchor date. Each anchor is subordinate to one of the case phases described in table I. Anchors 1–18 of one embodiment of the present invention are described in table II with the relevant case phase as follows:

TABLE II

| Phase | Anchor | Description |
| --- | --- | --- |
| PN | 1 | Date of Accident |
| PN | 2 | Date Client Retains Attorney |
| DIP (also PN) | 3 | Client Released From Treatment |
| N | 4 | Demand Sent |
| N | 5 | Date Mediation or Arbitration Hearing Set |
| L | 6 | Date File Marked Complaint Received |
| L | 7 | Plaintiff's 1st Set of Discovery Documents Sent |
| L | 8 | Plaintiff's 2d Set of Discovery Documents Sent |
| L | 9 | Plaintiff's Third Set of Discovery Documents Sent |
| L | 10 | Date Deposition Arranged by Plaintiff |

TABLE II-continued

| Phase | Anchor | Description |
|---|---|---|
| L | 11 | Date Deposition Taken/Schedules by Plaintiff |
| L | 12 | Deposition Taken by Plaintiff |
| L | 13 | Receipt of Defendant's Discovery Documents |
| L | 14 | Date Deposition of Plaintiff Arranged |
| L | 15 | Date Deposition of Plaintiff to Take Place |
| L | 16 | Date Deposition of Plaintiff Taken |
| L | 17 | Date of Receipt of Trial Date Setting |
| S | 18 | Case Settled |

Activation of "set/view client anchors" in window 172 generates a set/view anchors form which lists anchors that have been set for the client record and the respective anchor dates. Also, additional anchors may be set as required by selecting the appropriate anchor number from a pull-down menu and entering the anchor date from this form. The operation of anchors and the inter-relation to case phases is further discussed in connection with FIGS. 3–8. Anchors may also be removed or indicated as complete through activation of button icons provided on the view/set client anchor form. Notably, various forms and processes of the management program may automatically remove or set anchors without needing to resort to the set/view anchor form.

Selection of button icon 170h of client info form 150 displays "send a document" in window 172. By double clicking on "send a document" with mouse 44, a view/print document form is displayed which provides a scrollable list of various form documents that may be generated with the management program. Typically, these documents are customized by the management program by inserting designated information from the calling client record in specified fields of the document. The customized document may be pre-viewed and printed utilizing a merge function with the WORD 6.0 application. Many of these documents are associated with at least one data field of the client record and the preparation/delivery of the document is tracked in the client record. In fact, the client record is typically automatically updated to reflect when the document has been prepared. Also, various prompts and ticklers of the management program prompt the automatic assembly and delivery of many of these documents. By way of non-limiting example, a program may provide a tickler to generate a letter to request medical records from a medical provider.

When the tickler becomes active, this letter is assembled by combining data from the client record with a standard form from the document list. Indeed, the management program may set additional ticklers to automatically follow-up on the request as part of the automated assembly process. When the medical request letter is generated with the management program, the program provides for updating the client record to reflect preparation of the request letter. Updating in this manner reduces errors compared to conventional systems which require an operator to manually select and enter data to indicate the delivery of various documents relative to a client record. The view/print document form is the same form that may be reached by button icon from the "view client daily tickler" form.

Selection of button icon 170i of data group collection 170 displays "negotiation" in window 172. By selecting "negotiation" a negotiation form is presented which includes client record information relating to the nature of the client's injuries, recovery time, medical treatment, and any scarring that may have resulted from the injury. This form also permits data entry regarding negotiation correspondence and other particulars via various memo fields. This information is used to support a formulated negotiation position. If a letter has been sent to the opposing party demanding compensation, this "demand letter" may be quickly pre-viewed by activating a button icon in the negotiation form. This screen is useful to quickly inform the client's attorney about the client's settlement position when contacted by telephone by the opposing party. The negotiation form is indexed by client.

Selection of button icon 170j of data group collection 170 displays "Alternative Dispute Resolution (ADR)" in window 172. By activating this line, a form is displayed which indicates either an arbitration or mediation ADR type, and the location, date, and time of the ADR hearing (if one has been set). Phone numbers, note fields, and other pertinent information may be presented in this ADR form. A check box icon is included to indicate if the ADR hearing has already taken place and a button icon is provided which may be activated to set the hearing date. The ADR form is indexed by client.

Selection of button icon 170k presents a number of client record data groups concerning litigation in window 172. These litigation data groups include: (1) Litigation—General, (2) Litigation—Court Information, (3) Informal (paper) Discovery, (4) Depositions—Schedule, (5) Depositions—Records, (6) Non-party, (7) Trial, and (8) Litigation—Notes. Selection of "Litigation—General" displays a form that tracks various dates associated with litigation.

The Litigation—General form is indexed by client and includes a check box icon to indicate if an answer to a served complaint or a motion for enlargement of time has been received, and if so the date of receipt is included in a date field. This form also displays a date field corresponding to the date the complaint was filed and the date the complaint was marked filed. A check box icon field corresponding to whether the marked complaint has been received is also included, as is a date field showing the date the marked complaint was received from the court. This form further includes fields corresponding to the name and county of the court having jurisdiction over the matter. Also, data fields corresponding to the filing of Summary judgment motions by either party are included. The Litigation—General form includes data indicating whether summary judgment motions have been filed and the time and date of any hearing scheduled concerning such motions. This form also includes fields to indicate the time and date of a pre-trial conference. The time and date of trial is also displayed in this form. In addition, date fields corresponding to documents filed to request a trial date are included. Notably, the dates the requesting documents were prepared with the program are also recorded automatically in these date fields.

Selection of "Litigation—Court Information" generates a corresponding form that has data fields for the court name, address, judge, cause number, and defendant names. Selection of "Informal Discovery" generates a corresponding form that highlights information regarding various paper discovery items. The informal discovery form has fields reflecting whether informal discovery interrogatories or requests that have been filed and which party filed them. Also, dues dates, and any enlargement of time motions which have been granted are reflected in appropriate data fields in this form. This form is indexed by client and includes button icons to add and delete discovery items as needed.

Selection of the "Depositions—Schedule" group from window 172 generates a corresponding form which has data fields for the person being deposed (deponent), the address of the deponent, the location of the deposition, the court reporter hired to attend and prepare the transcript, and the time and date of the deposition. The court reporter data may be selected from a master list provided as a pull-down menu in this form. A check box icon indicating if the deposition was held is also provided. The depositions—schedule form is indexed by client.

Selection of the "Depositions—Records" group from window 172 generates a corresponding form which has data fields corresponding to the tracking of the transcript resulting from a deposition. When a client is deposed, the client is given and opportunity to review the transcript first and make corrections. Check box icons are provided in the depositions—records form to track receipt and review of an original transcripts by the client. Also, a check box icon is provided to indicate if a copy of the transcript has been received for all depositions that have taken place. This form also includes data fields to identify the person deposed, the deposition time/date/place, the reporter name, and text fields for the optional entry of notes.

Selection of the "Non-Party" group from window 172 generates a corresponding form which has data fields directed to the name, address, representation (if any), and telephone number of any third parties other than the client (plaintiff) and defendant. Selection of the "Trial" group from window 172 generates a trial form that tracks whether various trial pleading have been received and whether various documents have been filed with the court. This form also includes the pre-trial conference and summary judgment data fields presented in the Litigation—General form. Pleadings tracked by this form include despositive motions, preliminary and final witness and exhibit lists, proposed jury instructions, and motions in limine. Selection of the "Litigation—Notes" group from window 172 results in the presentation of a form with data fields showing the court name and county, the pre-trial conference information, and the summary judgment information previously discussed. This form also includes textual note fields and litigation document distribution description fields. Generally, all data groups selectable from window 172 in response to activation of button icon 172k are indexed by client.

Activation of button icon 170l displays "Check Information" in window 172, which, when selected, generates a form that highlights information about checks generated on behalf of the client. Typically, these checks are used to pay for expenses, costs, and fees incurred during the pursuit of the client's claim.

The forms displayed in response to selection of a data group listed in window 172 typically each include a number of common button icon options. These options include: (1) demand wizard, (2) defendant lookup, (3) the client log, and (4) an exit button. The demand wizard button icon is selected to generate a demand letter. Demand letter generation with the management program is further discussed in connection with scheduling routines 300 and 400 hereinafter. The defendant lookup button icon facilitates finding a record based on the defendant's name. The client log button icon accesses the client log previously discussed. The exit button icon returns to form 150 from the currently active form.

Generally, data groups 170 of form 150 provide access to a comprehensive collection of data for each client record which enables the efficient tracking of all stages of the client's claim. However, the day-to-day management of multiple client records is enhanced by the ability to collate actions needed to be taken on behalf of multiple clients on a daily basis.

Figure 2C:
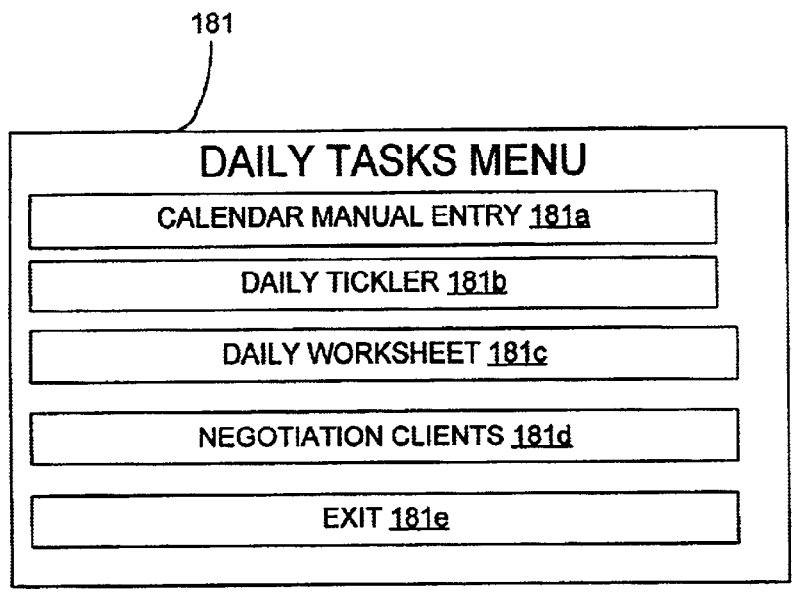

Referring back to FIG. 2A, button icon 101b is activated to select the Daily Tasks menu 181 as illustrated in FIG. 2C. Menu 181 is arranged to facilitate the prompt and efficient updating of a number of client records. Menu 181 includes button icon 181a which is activated to manually enter activities in a calendar table maintained by the management program. Menu 181 also includes button icon 181b which is activated to generate the daily tickler form previously discussed as an option in window 172 when button icon 170f of Client Info form 150 is activated. Selection of button icon 181c of menu 181 generates a daily worksheet which lists outstanding ticklers and other prompts, indicating actions that need to be taken to maintain advancement of all open client cases relative to a specified date. The scheduled generation of these ticklers and prompts to provide for the timely and efficient advancement of a client's claim from one phase to the next is further described in connection with FIGS. 3–8. The worksheet presents the clients in alphabetical order with the outstanding action items being indicated adjacent to the client name. When multiple action items exist, then the items are chronologically listed by the date action should be taken. This worksheet is typically printed using printer 54 to facilitate handling by the legal support staff of the attorney's office representing the client.

Button icon 181d is selected to generate a form that sequentially presents selected aspects of the client records in the negotiation phase. This dedicated negotiation form focuses attention of the legal support staff on this critical phase of the personal injury claim process. Exit button icon 181e is selected to return to main menu 101 from menu 181.

Figure 2D:
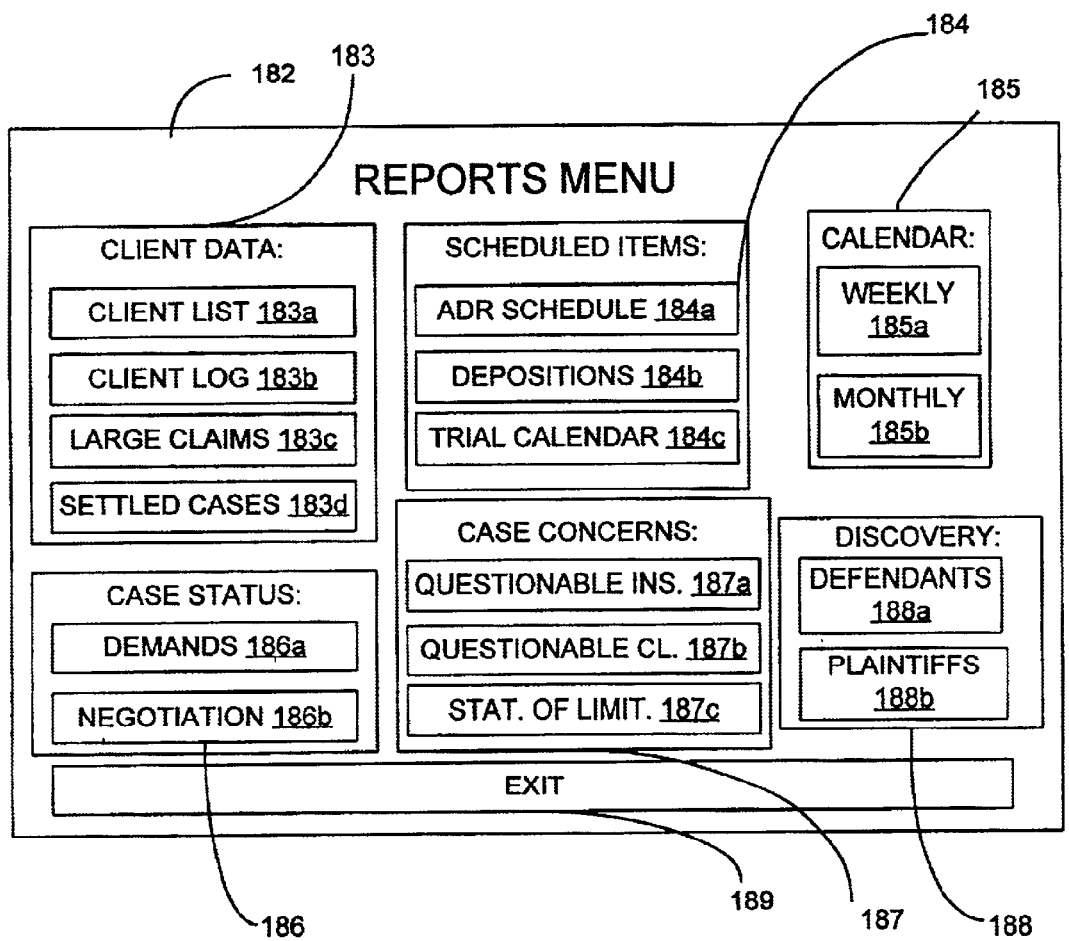

Main Menu 101 of FIG. 2A also includes button icon 101c which is selected to bring-up Reports Menu 182 depicted in FIG. 2D. Menu 182 provides for the selection of various reports organized by report group. Group 183 focuses on client data and includes button icon 183a to generate a report that alphabetically lists all open client records in accordance with case phase status. Group 183 also includes button icon 183b to select a comprehensive client log which includes the client activity log for every open client record alphabetically. Button icon 183c is included in group 183 to generate a report summarizing only those open client records having a large claim status. Group 183 also includes button icon 183d to generate a report summarizing selected aspects of settled cases.

Menu 182 also includes report group 184 which is directed to various scheduled meetings that require the attendance of the client's attorney. Group 184 includes button icon 184a which provides a report summarizing, in alphabetical order, selected aspects of client records with scheduled ADR hearings. Button icon 184b of group 184 is selected to provide a report of schedule depositions in alphabetical order by the name of the person who is the subject of the discovery. Button icon 184c of group 184 is selected to generate a Trial/ADR calendar from a selected date forward in chronological order.

Menu 182 includes report group 185. Group 185 has button icon 185a to generate a weekly calendar of scheduled events requiring attorney action for a one week period including a selected date. Group 185 also has button icon 185b to generate a monthly calendar in the same manner.

Group 186 of menu 182 provides reports directed to critical phases of client's claims. Button icon 186a of group 186 is selected to generate a report in alphabetical order of all clients in the Demand In Progress (DIP) phase. Prompt gathering of relevant information after a client is released from treatment is essential to the efficient advancement of a case from the pre-negotiation phase to the negotiation phase as highlighted by the report of button icon 186a. Button icon 186b of group 186 is selected to generate a report in alphabetical order of all clients in the negotiation phase to facilitate prompt and fair settlement.

Group 187 provides reports directed to claims which may be in jeopardy. Button icon 187a of group 187 is selected to provide an alphabetical report by client name of all claims where the insurance coverage is questionable. Button icon 187b of group 187 is selected to generate an alphabetical report by client name of all claims where the defendant's liability may be questionable. Button icon 187c of group 187 is selected to provide an alphabetical listing of claims where the statute of limitations is close to running out or may otherwise be an issue.

Group 188 provides reports relating to discovery. Button icon 188a is selected to provide a report summarizing discovery items by the defendant in alphabetical order by the client's name. When multiple discovery entries exist for the same client, the entries are in chronological order. Button icon 188b is selected to provide a report summarizing discovery items by the plaintiff in alphabetical order by the client's name. When multiple discovery entries exist for the same client, the entries are in chronological order. Exit button icon 189 is selected to return to main menu 101.

Menu 101 also includes button icon 101d which is activated to view data records that track the referral source of clients. The referral sources include various television programs, telephone yellow pages, and medical provider referrals. Button icons are provided to view master television, yellow page, and medical provider referral tables; and to generate a report that summarizes referrals by source type for a given date range. Menu 101 has button icon 101e which is activated to access various check writing and accounting functions provided by the management program. Menu 101 also has button icon 101f to present a system information menu concerning selected aspects of the program such as master tables of attorneys, documents, evidence items, court reporters, medical providers, and trial items. The system information menu also provides information relative to ticklers and anchors which are discussed further in connection with FIGS. 3–8.

Returning to FIG. 2, during process 110, the management program schedules a number of prompts (including selected ticklers) in various stages relative to an active anchor date. The prompts are presented to an operator of the management program such as the client's attorney or legal support personnel via one or more of output devices 50. The management program is configured to maintain anchor schedules for each client record independent of the others. Notably, the various anchors may be initiated on different dates for different client records, requiring the management program to independently maintain the anchor schedules for each client record. For each anchor, the management program generally executes as series of related prompts that are generally directed to promoting various actions to advance each client's claim through pre-negotiation, negotiation, and on to settlement. Typically, the operator responds to these prompts by providing an input with one or more of input devices 40 or takes such other action as directed. Generally, once an entry is made in a client's record that satisfies a given prompt, follow-up prompts related to the data entry are considered completed and further presentation is accordingly suppressed. Once all prompts for a given anchor are completed, the anchor is considered complete.

If prompted to send a letter to a party, the management program is typically configured to offer the operator the option of generating the letter with the program by merging appropriate information from the client record with a form letter from the documents table. The letter may be printed with printer 54. Furthermore, the management program typically updates appropriate fields in the client data record which may initiate further prompts or ticklers to advance the client's case. As responses to letters and other prompted actions are received, the information is entered into the client's record as appropriate. Generally, status of the client records advance as the various prompts are addressed. A case phase change for a given client record typically corresponds to the initiation of a corresponding anchor via the management program.

Process 110 begins with stage 112. In stage 112 anchors 1 and 2 are concurrently activated. For anchor 1, the anchor date is the date of the accident. Anchor 1 is directed to assuring that the complaint is filed before expiration of the statute of limitations time period. Specifically, in response to setting anchor 1, the management program prompts a review of the client's file for non-parties that should be added to the complaint as defendants and prompts creation of a complaint (if none was previously filed) or prompts amendment of a previously filed complaint 510 days after the date of accident. This 510 day time period is selected in accordance with the applicable statute of limitation which may differ with the pertinent legal jurisdiction. A second prompt is provided 20 days later (530 days after the complaint) prompting inquiry into whether the complaint or amended complaint with a filing stamp of the clerk of the court has been received by the attorney. If not, the operator is prompted to telephone the court or re-file the complaint.

Anchor 2 has an anchor date of the day the attorney is retained by the client. Scheduling routine 200 of FIGS. 3A–3D further details the operation of anchor 2. Routine 200 starts when the anchor 2 date is entered, triggering a number of prompts in accordance with a schedule spanning several days. The management program is configured to independently execute routine 200 for each client record when anchor 2 and the corresponding anchor 2 date are set for a client record.

Figure 3A:
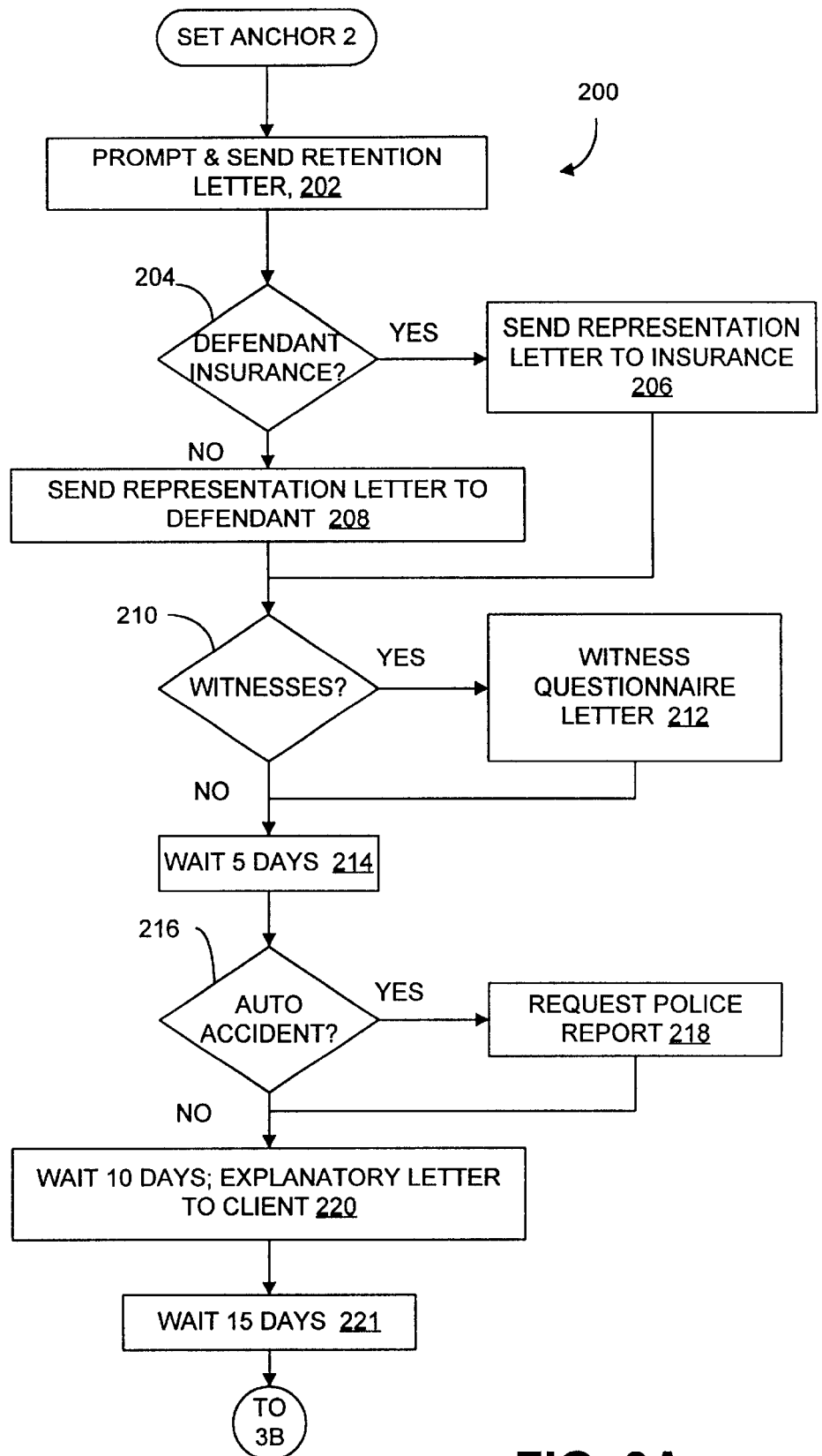
FIGS. 3A–3D present a flow diagram depicting scheduling routine 200 to manage selected aspects of stage 114 shown in FIG. 2.

Referring to FIG. 3A, operation 202 of routine 200 presents a prompt to generate a letter to the client indicating that the attorney has been retained by the client. Next, conditional 204 is encountered which tests whether the defendant to the client's injury is represented by insurance. If so, then the operator is prompted to send a notice of representation to the defendant's insurer in operation 206. If the defendant does not have an applicable insurance carrier, then the operator is prompted to send a notice of representation directly to the defendant in operation 208. At conditional 210, the operator is prompted to determine whether there are any witnesses to the incident resulting in the client's injury. If so, then in operation 212, the operator is prompted to generate and forward a witness questionnaire letter to each witness. The questionnaire letter may be generated at the operator's discretion.

The program then times the lapse of 5 days from the anchor 2 date in block 214. Once this period has lapsed the program prompts whether the injury resulted from an automobile accident via conditional 216. If so, the program prompts the request of a police report in operation 218. The program awaits the passage of a total of 10 days from the anchor 2 date in operation 220 and prompts the preparation of an explanatory letter for the client.

Figure 3B:
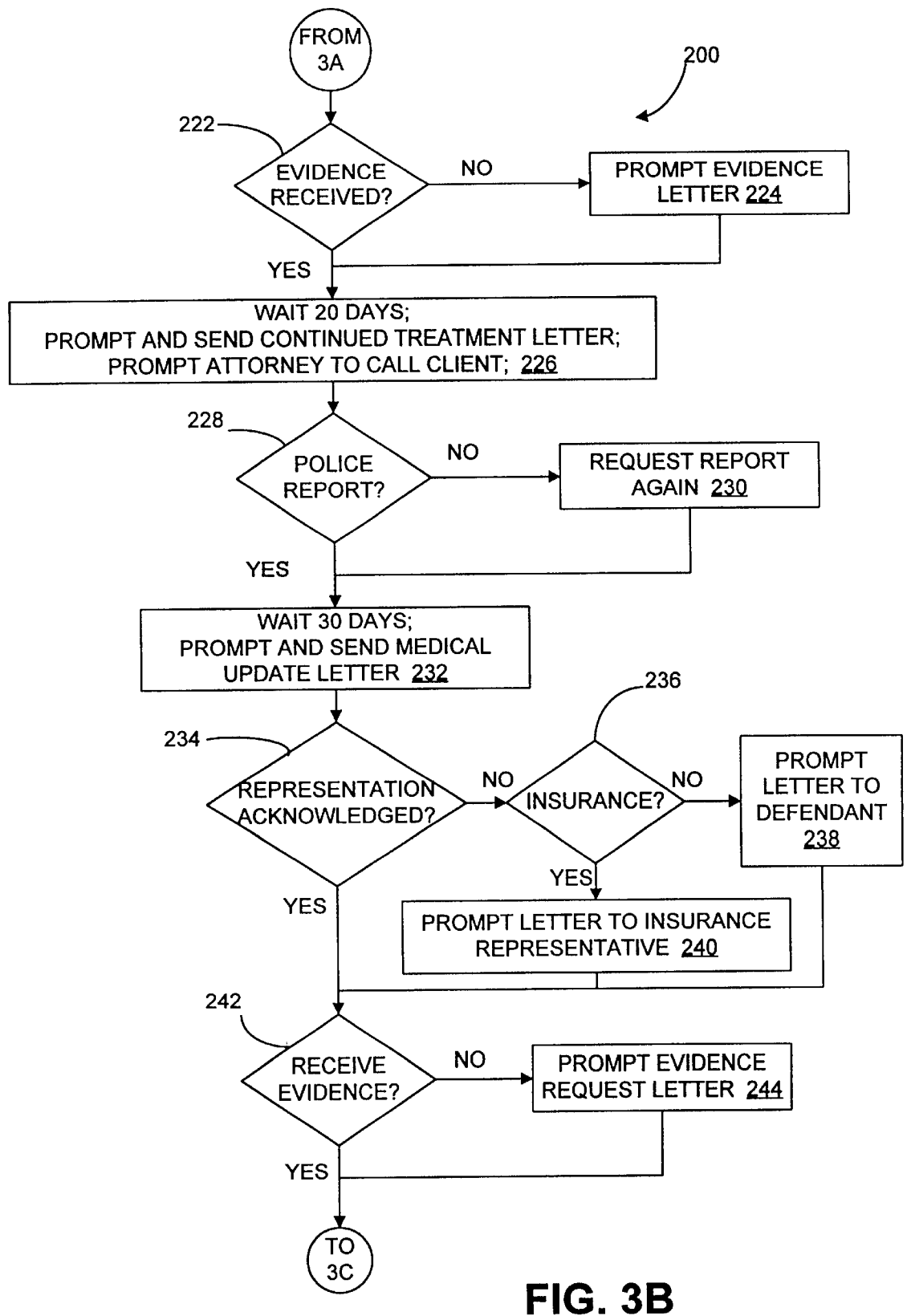

Next the program waits a total of 15 days from the anchor 2 date in accordance with block 221. Referring to FIG. 3B, conditional 222 is executed at the 15 day mark. Conditional 222 prompts an inquiry into whether evidence has been received from the client. If not, the operator is prompted to generate and send an appropriate request letter to the client in operation 224. The program then waits for 20 days to lapse from the anchor 2 date in operation 226. At the 20 day point, operation 226 prompts generation of a letter reminding the client to continue treatment as appropriate. Operation 226 also prompts the attorney to call the client to review the case. Control flows to conditional 228 to determine whether a requested police report has yet been received in response to operation 218. If not, a second request is prompted in operation 230.

Control then flows to operation 232 where the program times a total of 30 days from the anchor 2 date. At the 30 day mark, operation 232 prompts generation of a letter to the client inquiring into the physical condition of the client and to determine if the client has changed medical providers. Conditional 234 follows, which prompts the determination of whether the attorney's representation has been acknowledged by the party receiving the notice in either operation 206 or operation 208. If not, then conditional 236 determines if there is an insurer for the defendant. If the defendant does not have insurance, then a second letter to the defendant is prompted in operation 238. If the defendant is insured, then a second letter to the insurance representative is prompted in operation 240. Control flows to conditional 242 from operations 238, 240 which again prompts to determine whether evidence has been received from the client. If evidence has not been received, then another evidence request letter is prompted in operation 244. It should be understood that such additional request letters are automatically customized to list only those evidence items that have not yet been marked as received from the client in the corresponding client record.

Figure 3C:
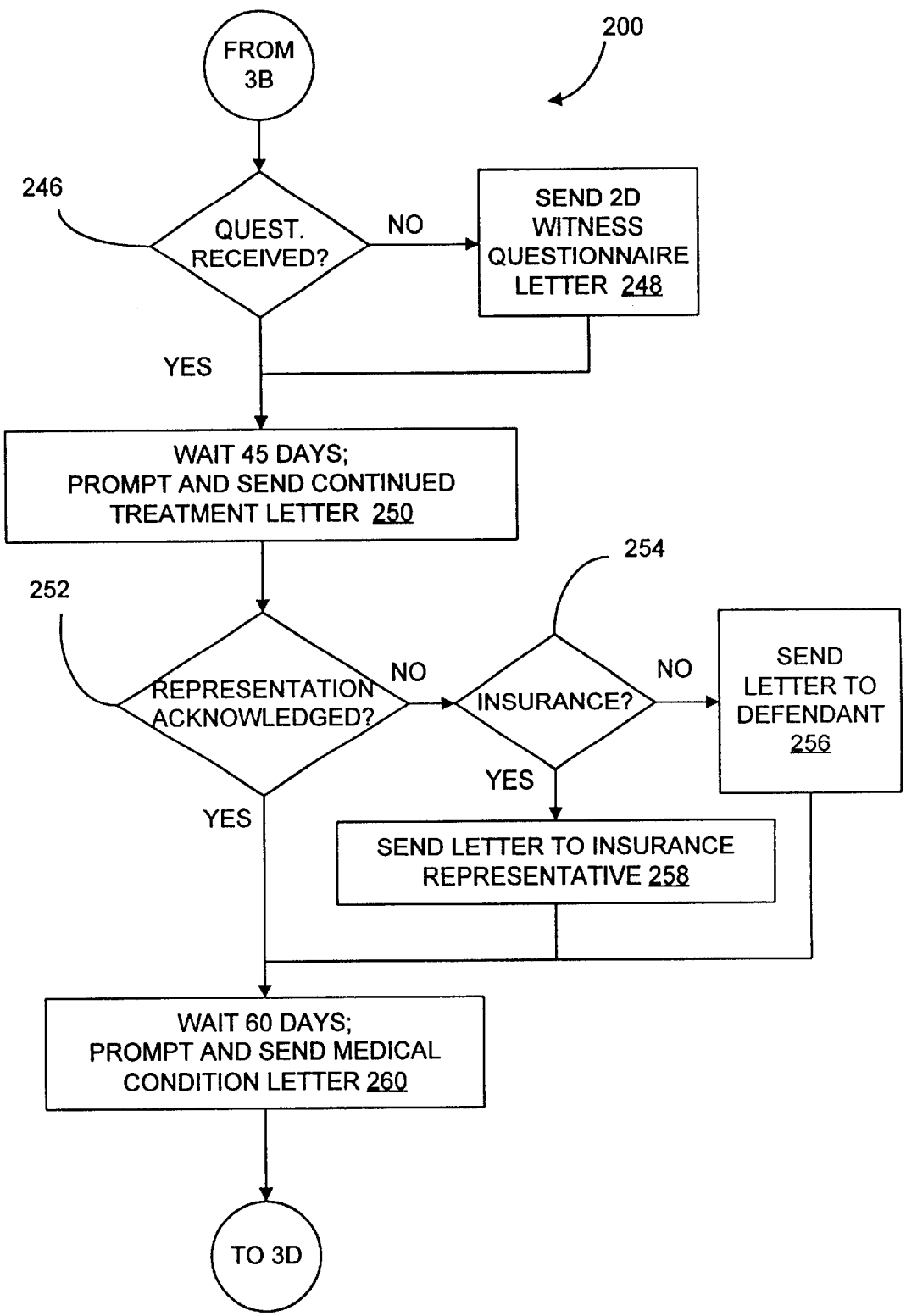

Referring to FIG. 3C, conditional 246 is next encountered, which again prompts whether the witness questionnaire has yet been received. If the questionnaire has not been received, then operation 248 prompts the generation of a second questionnaire request letter. Operation 250 is next encountered, which waits until 45 days lapse from the anchor 2 date before taking action. Once the 45 day period has lapsed, operation 250 prompts a letter to the client reminding the client to continue medical treatment. Also, a conditional to determine acknowledgement of representation is again encountered in conditional 252. If there is not acknowledgement, then conditional 254 tests whether the defendant is insured. If not insured or otherwise represented, another letter to the defendant is prompted in operation 256. If the defendant is insured, then operation 258 prompts generation of another letter to the representative.

Figure 3D:
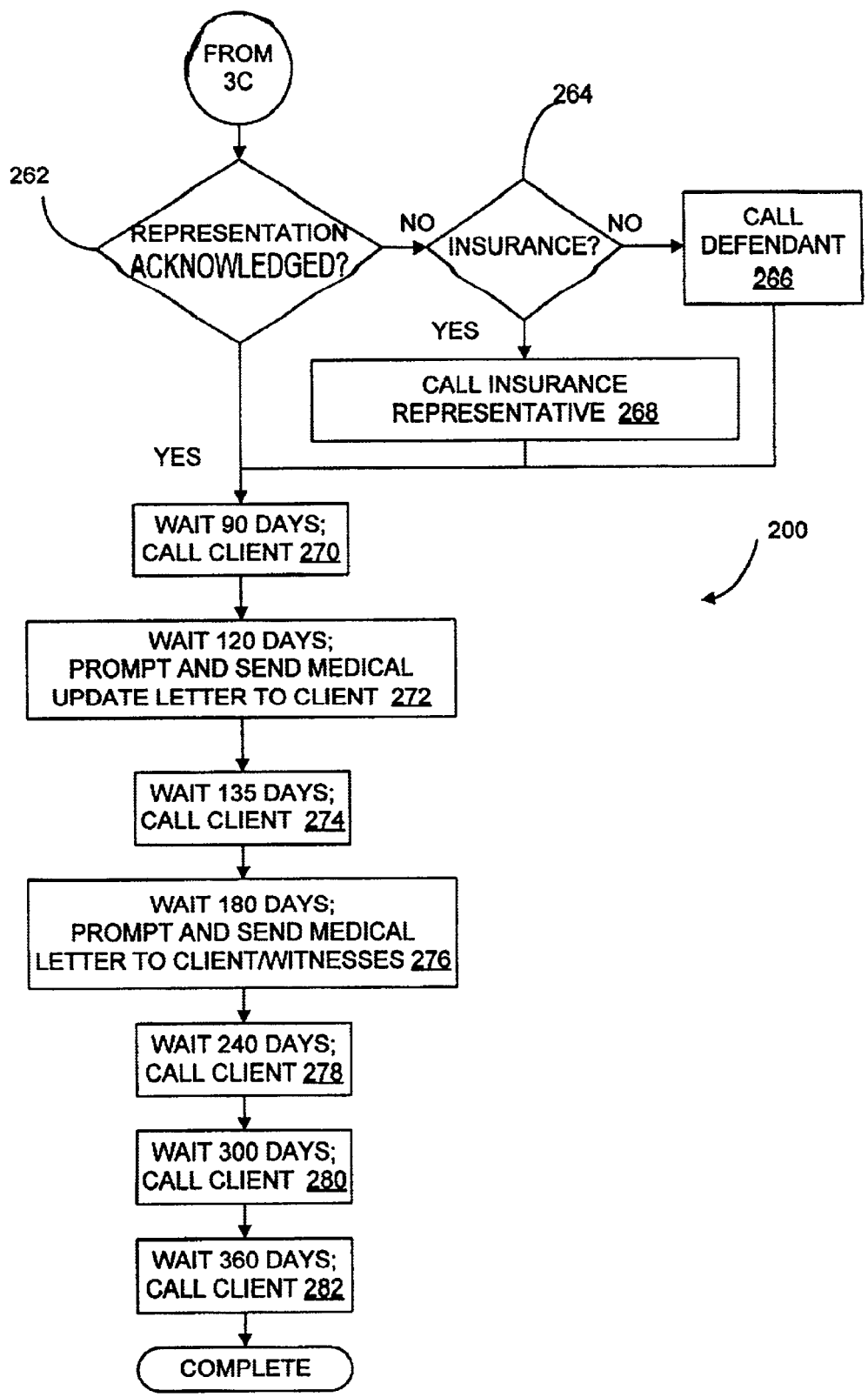

Operation 260 is next encountered which times the lapse of 60 days from the anchor 2 date, then prompts a letter to the client inquiring into the client's medical condition and whether any change in medical providers has occurred. Referring to FIG. 3D, conditional 262 is then encountered which prompts to determine whether representation has yet been acknowledged. If there has been no acknowledgement still, then conditional 264 tests whether the defendant is insured or has other representation. If the defendant is not represented, then the attorney is prompted to telephone the defendant in operation 266. If the defendant is represented, then the attorney is prompted to call the representative in operation 268.

Operation 270 is next encountered which waits until 90 days lapse from the anchor 2 date, then prompts the attorney to telephone the client to review the case. In operation 272, after 120 days have lapsed, the program prompts the generation of a letter to the client to inquire into the client's physical condition and whether there has been a change of medical providers. After 135 days from the anchor 2 date, operation 274 prompts the attorney to telephone the client to discuss the case. In operation 276, a letter to the client is prompted inquiring into the client's medical condition and medical provider status. At intervals of 240, 300, and 360 days from the anchor 2 date, the attorney is prompted to call the client in operations 278, 280, 282, respectively. Operations for routine 200 are then completed.

Anchor 3 is initiated with the release of the client from medical treatment, and is set to the client's medical release date, corresponding to stage 116 of process 110 (see FIG. 2). Scheduling routine 300 of FIGS. 4A and 4B details the operation of anchor 3. Routine 300 begins with operation 302 which prompts generation of a letter to the client for an inventory of the client's medical treatment during anchor 2. A request for a copy of medical records of known medical providers is also prompted in operation 302. Conditional 304 is next encountered which prompts the determination of whether the client missed work as a result of the injury. If work was missed, then operation 306 prompts a request to the client's employer for a statement of the client's lost wages. Control flows to conditional 308 which tests whether the client's injury was of a serious nature. If the injury was serious, then a narrative from one or more medical providers is prompted in operation 310.

Next, the program times an interval of 10 days from the anchor 3 date (medical treatment release date) in block 312. Conditional 314 is encountered at the 10 day point which prompts whether the medical inventory letter prompted in operation 302 has been received. If the inventory letter has been received, then a request of a copy of medical records from previously unknown medical providers is prompted in operation 316. In operation 318, the attorney is prompted to telephone the client and meet with the client as required. The program then times the lapse of 20 days from the anchor 3 date in block 320.

Figure 4A:
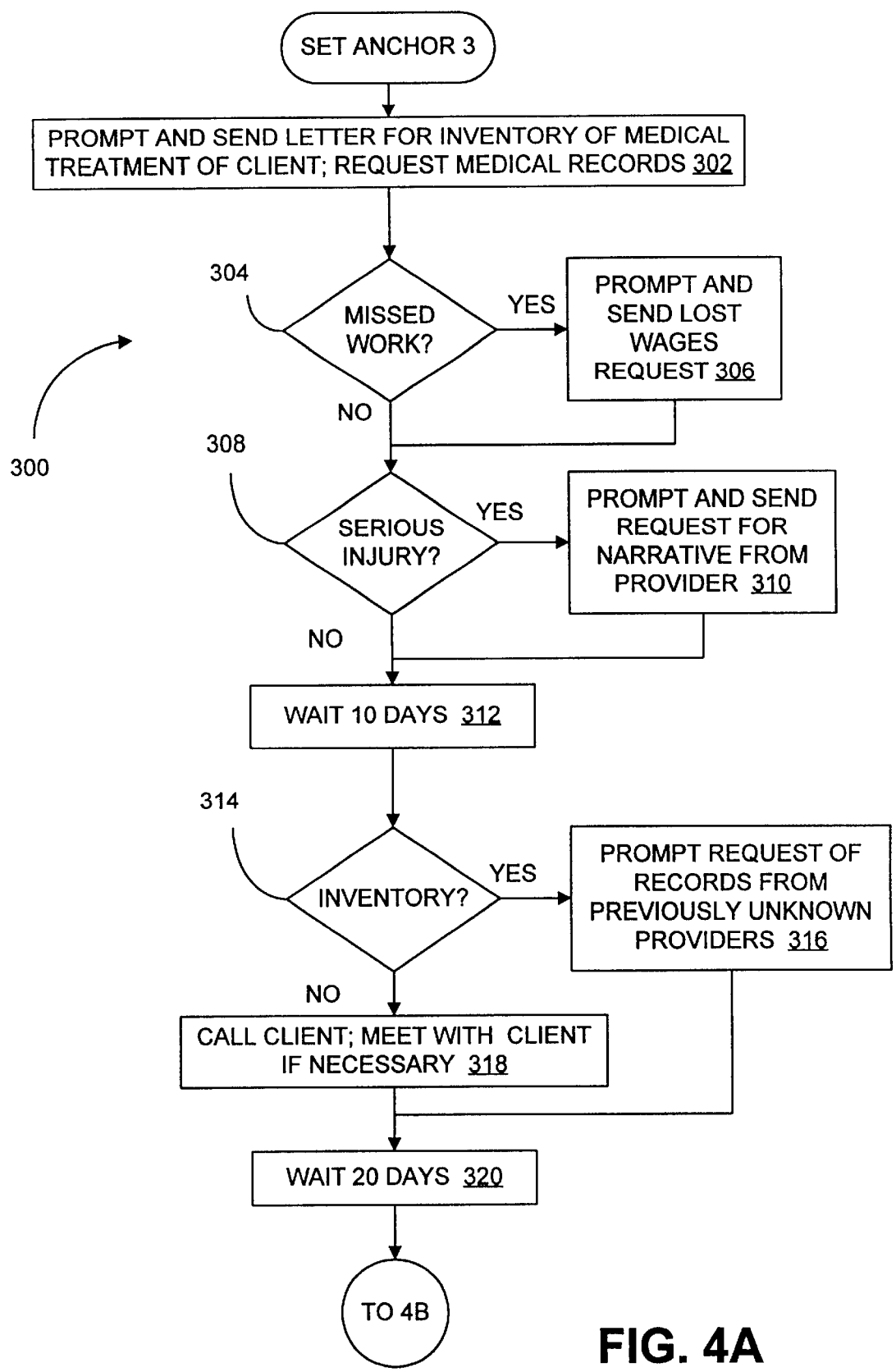
FIGS. 4A–4B present a flow diagram depicting scheduling routine 300 to manage selected aspects of stage 116 shown in FIG. 2.
Figure 4B:
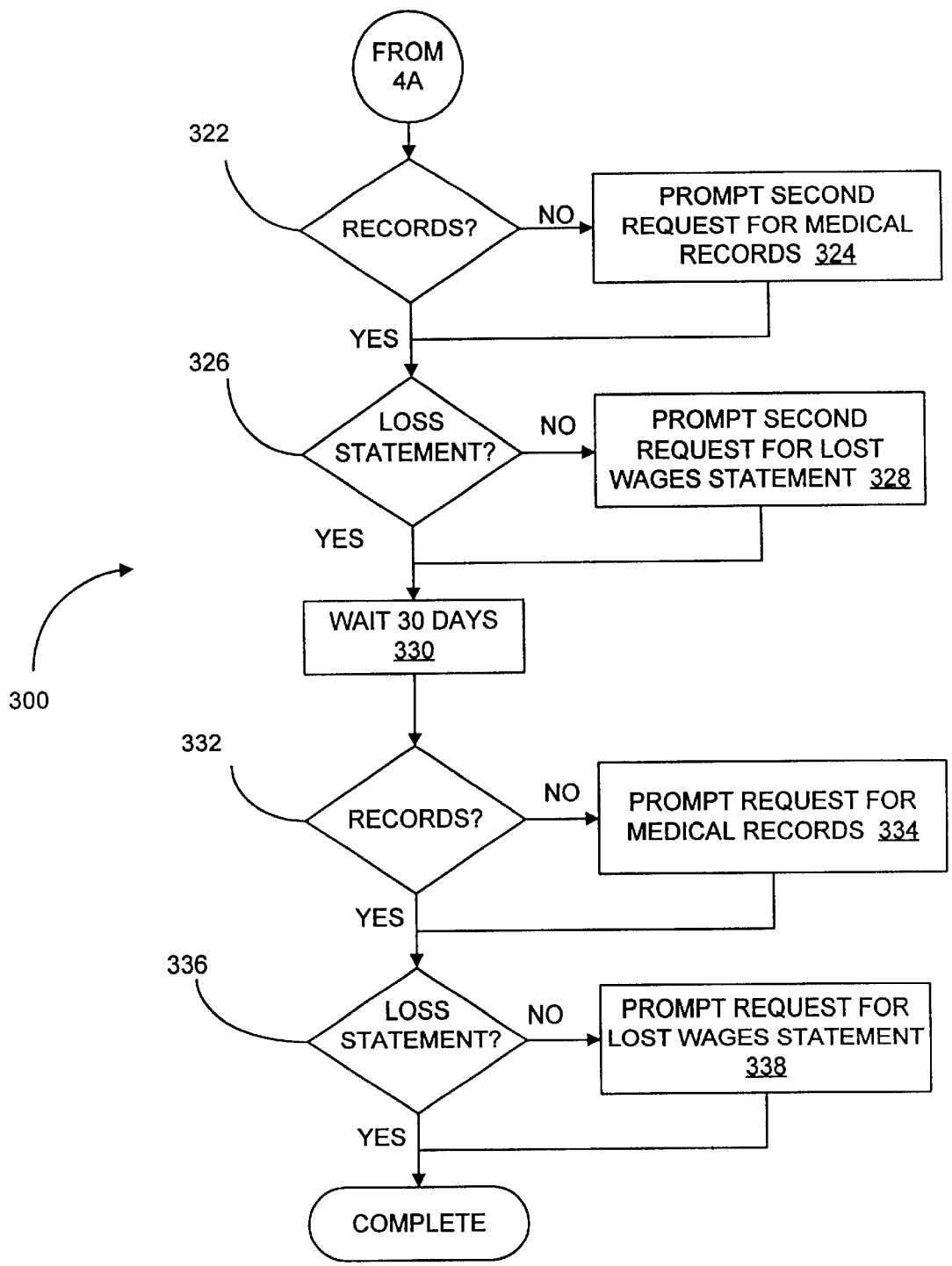

Referring to FIG. 4B, conditional 322 is encountered at the 20 day point. Conditional 322 prompts to determine whether medical records have yet been received. If the medical records have not been received, then operation 324 prompts a second request letter to the medical providers who have not responded. Conditional 326 is also encountered at the 20 day point to follow-up on the lost wages statement requested in operation 306. Control then flows to block 330 where the program times a total lapse of 30 days from the anchor 3 date. Conditional 332 is next encountered which prompts the determination of whether the medical records requested in operations 302, 316, 324 have yet been received. For records not yet received, a request is prompted in operation 334. Conditional 336 inquires again into whether the lost wages statement has yet been received from the employer as requested in operations 306, 328. If not received, another request for the lost wages statement is prompted in operation 338. The operations of routine 300 and anchor 3 are then complete.

Anchor 4 is initiated by sending a demand letter to the defendant or the defendant's representative, corresponding to stage 118 of process 110 (see FIG. 2). The satisfaction of prompts and information targeted for collection under anchors 2 and 3 generates a prompt to initiate preparation of a demand letter by the operator. The program assembles this letter from information entered by the operator in response to prompts of anchors 2 and 3 through the execution of routines 200 and 300. The program further assembles the letter from a standard form and paragraphs that are selected or customized by the operator through a demand letter wizard operation. Also, the program also automatically performs calculations to account for all expenses, costs, and other damages in formulating a proposed compensation amount for inclusion in the demand letter.

Once demand letter preparation is selected, the demand wizard provides a selectable sequence of displays to assemble the letter. The program begins with an explanatory form, then advances to present a standard introductory paragraph in another form which may be altered as required. In the next form, a paragraph may be composed to relay personal details concerning the client which are deemed to be persuasive in achieving the desired settlement amount. A custom paragraph details facts concerning the accident that caused the injury is next prompted by a corresponding form. A paragraph directed to the applicable law is next composed or selected from a pull-down menu of form paragraphs. Next, a paragraph detailing the client's course of treatment is authored. A treatment cost reconciliation form is then presented which directs the operator to verify medical provider bills before medical costs will be calculated for inclusion in the demand letter. A default paragraph regarding intangible damages is next presented by form that may be altered as needs require. Next, a paragraph summarizing the client's loss of earnings is prompted by form. The program calculates and inserts amounts corresponding to lost wages and loss of opportunity resulting from the injury as previously gathered during anchors 2 and 3. A standard paragraph directed to lost wages law is then provided by form which may be altered as required. The next form presented prompts the operator to select from among several other types of damages not yet quantitized, including: (1) pain and suffering, (2) loss of enjoyment of life, (3) permanent impairment, (4) mental anguish, (5) travel to/from medical treatment, and (6) loss of spousal services. The operator is prompted to assign compensation amounts to the selected damage types added from this list. The operator is then prompted to preview or print the letter with the automatically calculated total proposed settlement amount.

Figure 5A:
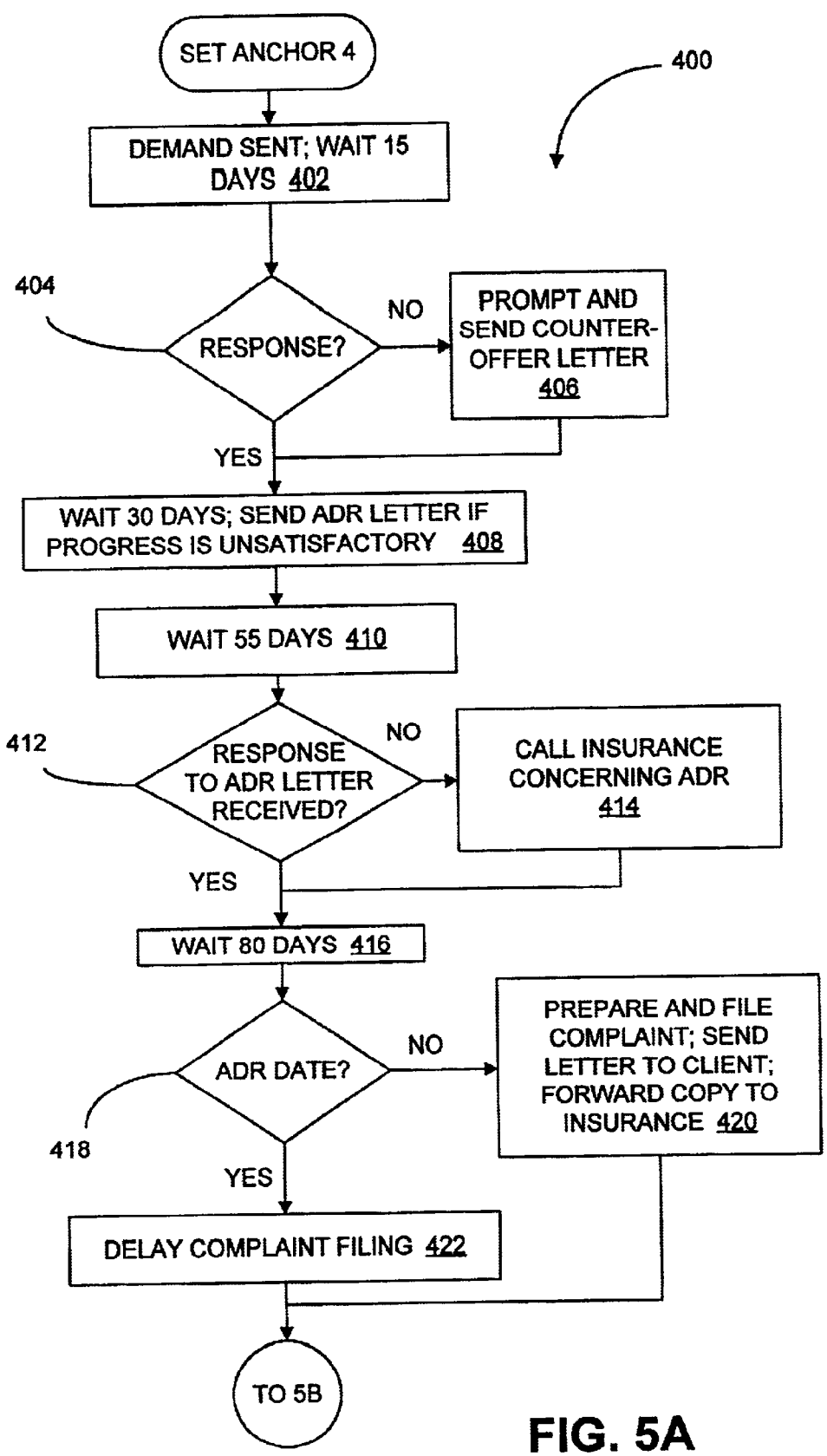
FIGS. 5A–5B present a flow diagram depicting scheduling routine 400 to manage selected aspects of stage 118 shown in FIG. 2.
Figure 5B:
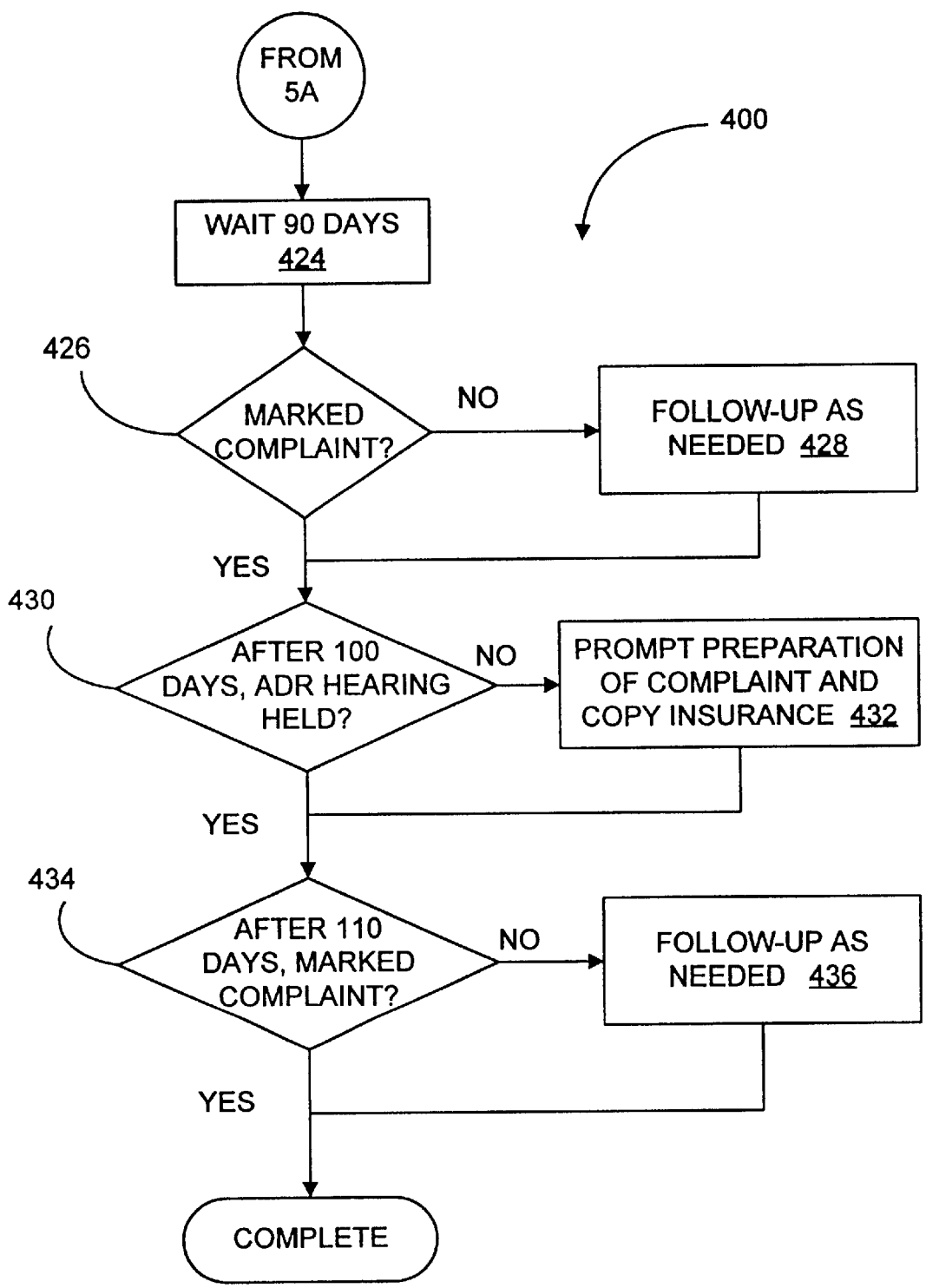
Figure 6:
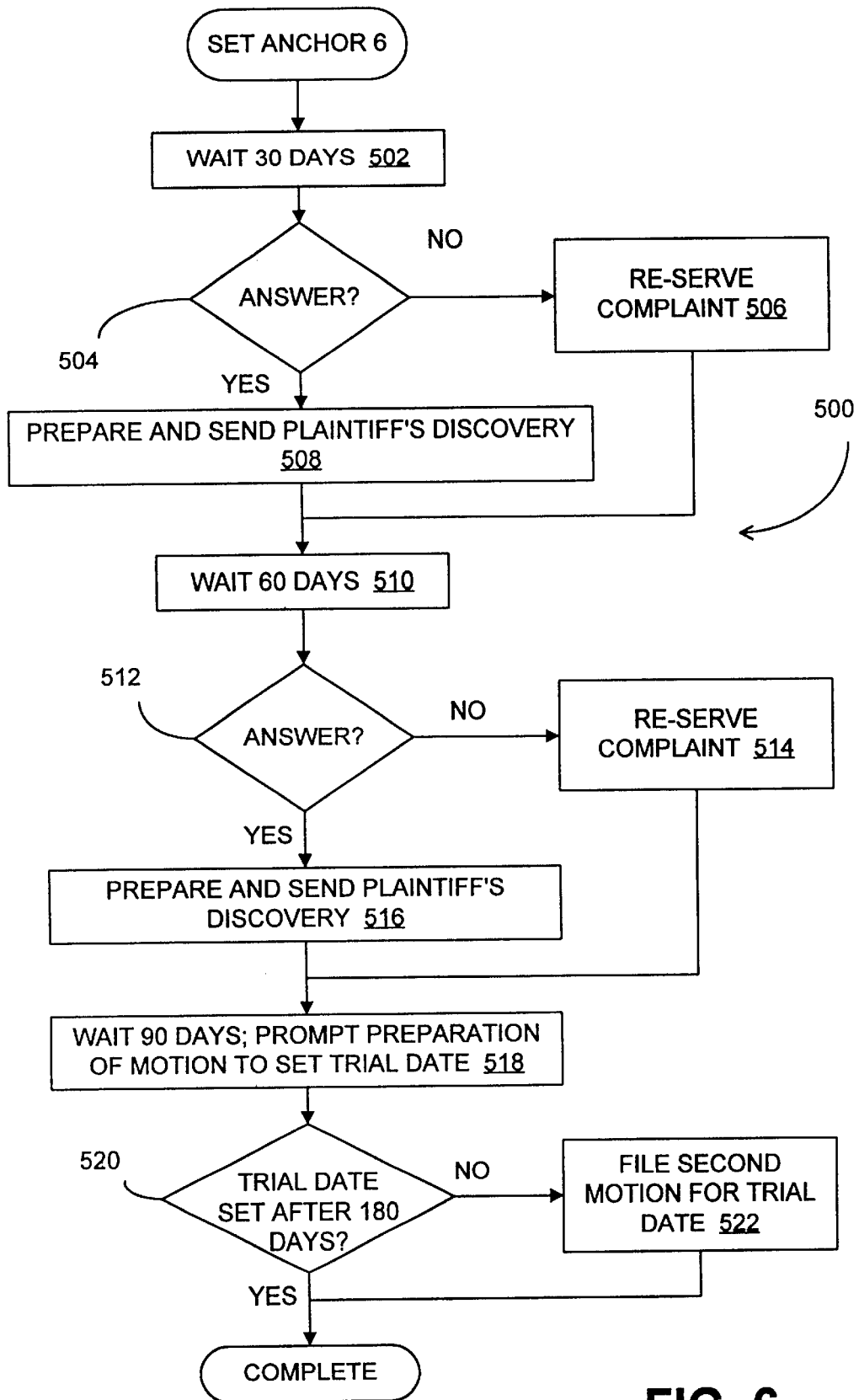
FIG. 6 presents a flow diagram depicting scheduling routine 500 to manage selected aspects of stage 130 shown in FIG. 2.
Figure 7A:
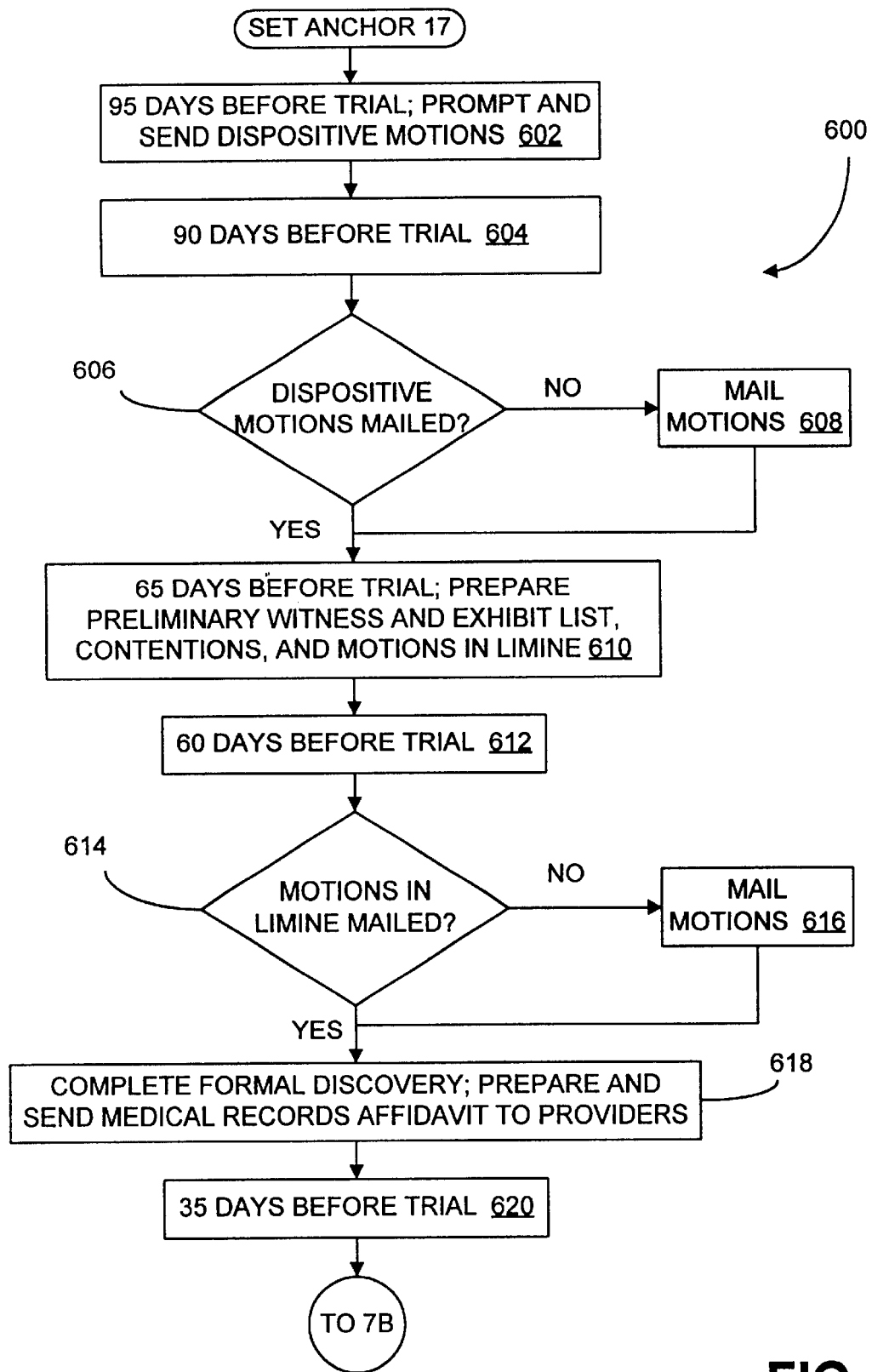
FIGS. 7A–7B present a flow diagram depicting scheduling routine 600 to manage selected aspects of stage 130 shown in FIG. 2.
Figure 7B:
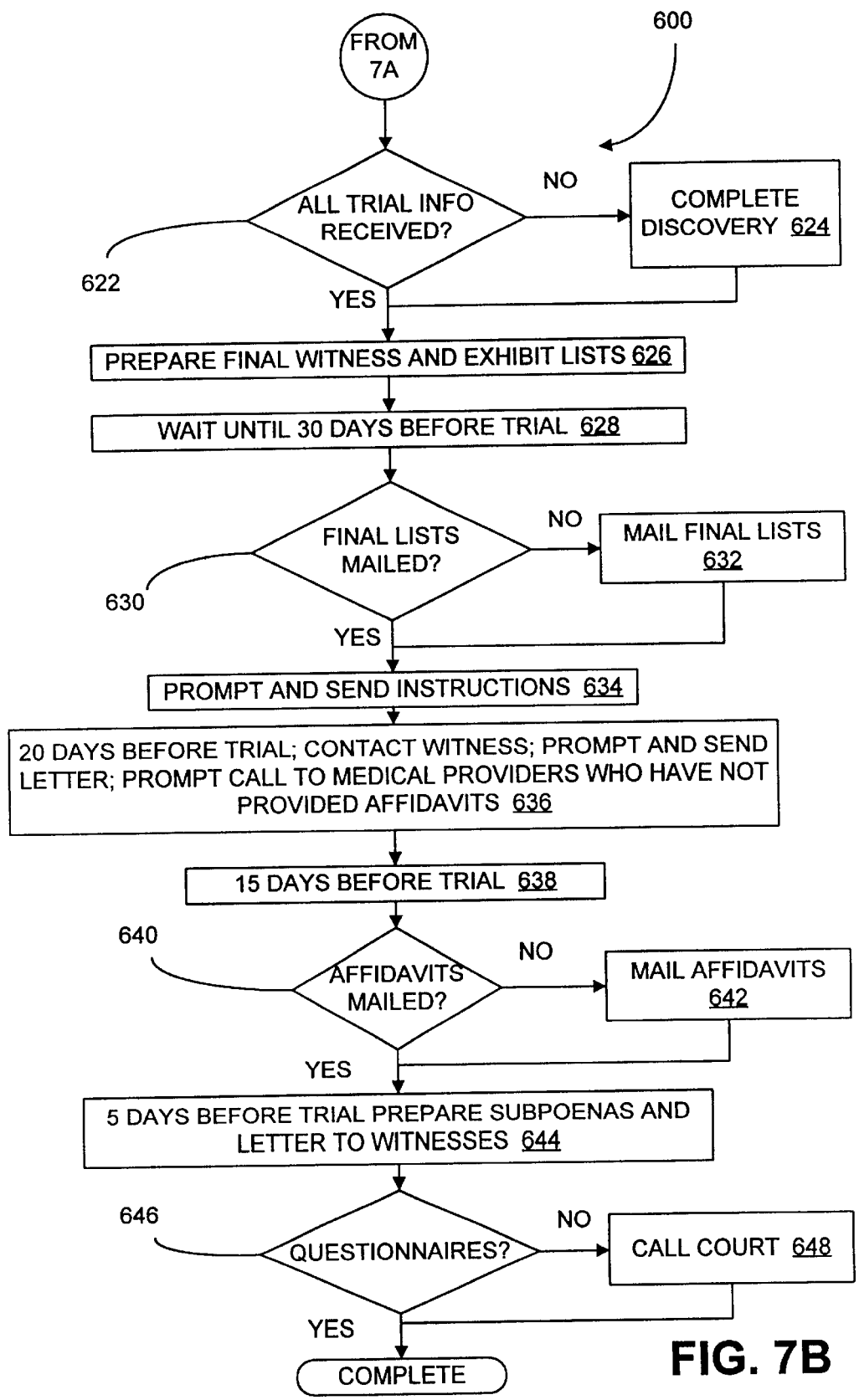

Once the demand letter is prepared, the operator is prompted to set anchor 4 which moves the case to the negotiation phase and automatically sets appropriate prompts associated with negotiation of the claim. Scheduling routine 400 details the operation of anchor 4 as illustrated in FIGS. 5A–5B. Referring to FIG. 5A, an interval of 15 days from the sending of the demand lapses in block 402. At this 15 day point, conditional 404 is encountered to determine whether a response from the defendant or defendant's agent has been received. If no response has been received, then operation 406 prompts generation of a letter inquiring into whether to expect a counter-offer to the demand. Control flows to operation 408 which times a total of 30 days from the anchor 4 date, then prompts delivery of a letter to the defendant or defendant's representative to propose an Alternative Dispute Resolution (ADR) process (such as arbitration or mediation) if no response to the demand has been received. Block 410 represents the lapse of 55 days from the anchor 4 date. At the 55 day point, conditional 412 is executed which tests whether a response to the ADR letter prompted by operation 408 has been received. If no ADR response has been received, then the attorney is prompted to call the defendant's representative in operation 414. A lapse of 80 days from the anchor 4 date is timed in block 416. At this 80 day point, a determination of whether an ADR date has been set is provided by conditional 418. If no date has been set, then the preparation and filing of a complaint to initiate a lawsuit on behalf of the client is prompted in operation 420. Copies of the complaint are forwarded to the client and defendant's representative in operation 420 as well. On the other hand, if an ADR date has been set, then the complaint filing is delayed in operation 422.

Referring to FIG. 5B, a lapse of 90 days from the demand date is timed in block 424. At this 90 day point, conditional 426 prompts to determine if a copy of a complaint, previously filed with the court on behalf of the client, has been returned with the filing date stamp. Conditional 426 verifies that the lawsuit process has been initiated. If the marked copy of the complaint has not been received, then operation 428 prompts follow-up action with the court in a few days. Conditional 430 is next encountered which checks whether an ADR hearing was held after a total lapse of 100 days from the anchor 4 date. If an ADR hearing was not held, then a complaint is prepared and filed, with copies to appropriate parties via operation 432. Also at the 90 day point, conditional 434 prompts to determine if a marked complaint, previously filed, has been received after the lapse of a total of 110 days from the anchor 5 date. If the marked complaint has not been received, then a follow-up in a few days is prompted by operation 436. The operations of routine 400 and anchor 4 are then completed.

Returning to FIG. 2, conditional 124 of loop 120 is encountered. Conditional 124 test whether settlement has been reached. If settlement has been reached, then control flows to stage 125 to finalize settlement. When the case is settled, the management program sets anchor 18 with the settlement date and a corresponding schedule of prompts are provided. These prompts include prompting an operator to determine whether settlement documents have been received ten days after the anchor 18 date. If the documents have not been received, a telephone call to the defendant's representative is prompted. If the settlement documents have been received, then a telephone call to the client is prompted. Next, the program times a lapse of 30 days from the anchor 18 date and then prompts to determine if settlement pleadings have been received. If the settlement pleading have not been received within 30 days, a call to the defendant's representative is prompted, otherwise a prompt to close and purge the client's file is generated. The settlement process ordinarily concludes with the delivery of a check in an amount agreed upon in reaching the settlement. This check is deposited and various client expenses, costs, and fees are then paid from the settlement proceeds.

Another feature of the present invention is the computerized accounting and disbursement of payments to various parties from the settlement proceeds. One embodiment of this technique is described in connection with the diagrammatic representation of workform 801 shown in FIG. 9. Workform 801 may be displayed in response to the selection of the Workform data group displayed in window 172 when button icon 170a of client info form 150 is activated (see FIG. 2B and accompanying discussion). Workform 801 includes client data area 802 which displays selected data fields from the client's data record, such as the client's name, client number, and telephone numbers. Also, it is preferred that data area 802 display case phase and indicate whether the client's claim includes uninsured or underinsured motorist coverage. The remainder of the data presented or entered in workform 801 is indexed by client.

Workform 801 has various viewing options which are activated by button icons 804a–804e. Window 810 displays various sets of data in response to activation of a corresponding button icon. Also, display block 806 indicates the contingent fee percentage charged by the attorney, and display block 808 indicates the corresponding dollar amount of the attorney's fee. The data fields of workform 801 are part of the client data record, being generally indexed by client.

When button icon 804*a* of workform 801 is activated, window 810 sequentially displays information pertaining to each defendant from which settlement is sought. This information includes the defendant's name and "mail to" destination. A data field for the settlement amount is included for each defendant with corresponding check box icons to separately indicate the receipt and deposit of a respective settlement check. It should be understood that this information is part of the client's data record and is typically entered earlier in other forms of the management program and collected in the workform to facilitate the settlement procedure.

Selection of button icon 804*b* displays information concerning expenses paid by the attorney on behalf of the client in window 810. Window 810 sequentially displays each expense item, including a description of the expense item, the party paid, and the amount paid. The information for each item also includes a check box icon to indicate whether a check was printed with the program, and a check box icon to indicate whether to include the expense in the settlement calculation.

Selection of button icon 804*c* displays medical provider information in window 810. A set of information for each provider is sequentially displayed.. This information set includes data fields corresponding to the identity of the provider, the provider phone number, the treatment cost and the amount of this cost to include in the settlement calculation. For each provider information set, a check box icon is included to verify the amount to include in settlement. The set also includes a check box icon to indicate whether to include the provider item in a itemized settlement breakdown that is forwarded as part of a letter to the client. Each provider set has a further check box icon to indicate whether a check needs to be written to the medical provider from the settlement proceeds.

Selection of button icon 804*d* displays subrogation/lien information in window 810. A set of information is presented for each subrogee or lienholder. Typically, the subrogee is the client's insurance company who has paid the client at least a portion of the amount sought from the defendant's insurance company. This information includes a radio button icon selection to show whether a subrogation or lien is involved and identifies the subrogee or lienholder accordingly. A data field for the amount of the claim of the subrogee or lienholder and a data field of the amount paid are also displayed for each set. Several check box icons are included in each information set. One of these check box icons is used to confirm whether to write a settlement check to the corresponding subrogee or leinholder and another of these box icons is used to confirm whether to include the item in the itemized settlement breakdown description. The management program automatically reduces the amount paid to the subrogee/lienholder by a percentage to the paid to the attorney.

Selection of button icon 804*e* displays information relating to uninsured motorist (UM) and underinsured, motorist (UIM) coverage in window 810. Typically, this coverage is provided by the client's own insurance and operates as a source of compensation for the client. An information set is provided for each policy. Each set includes fields to identify the insurer and the settlement amount. The set also includes a check box icon to indicate receipt of the check for the UM/UIM settlement and another check box icon to indicate the UM/UIM settlement check has been deposited.

Button icon 812 is selected to generate a settlement letter which is forwarded with a check for the client's share of the settlement proceeds. This letter includes the itemized settlement breakdown of all compensation (settlement) sources; and expenses, costs, and fees paid on behalf of the client. The program automatically calculates the amount paid to the client from these accounting entries. Button icon 812 will not permit generation of the letter until all outstanding settlements have been deposited (defendant, underinsured motorist, and uninsured motorist claims) and all amounts owed by the client are ascertained and verified. Button icon 814 is selected to preview checks which may be generated with the program. Button icon 816 is selected to generate checks to pay all debts of the client owed from the settlement amount and to provide the client their share of the settlement proceeds. Password access is required to generate settlement checks through the selection of button icon 816. Similar to the generation of a settlement letter, the generation and printing of settlement checks with button icon 816 requires that all settlements and amounts owed be finalized and verified. Button icon 816 initiates routines that examine the accounting entries and confirm that all relevant accounting entries from the settlement, expenses, providers, subrogation, and UIM information sets have been verified. These routines display a summary of unverified items which must be confirmed by the operator before the system will allow settlement checks to be generated.

Workform 801 provides an efficient technique to calculate and disburse settlement proceeds with a considerable reduction in the chances of error compared to conventional methods. It should be understood that the information presented in as workform 801 is a part of each client record and may readily be utilized as the workform described in connection with FIG. 2B.

Referring back to FIG. 2, if conditional 124 is not satisfied, then conditional 126 is encountered which tests whether an Alternative Dispute Resolution (ADR) hearing is set to be held. If an ADR is being formed, then operation 127 corresponds to the execution of number of prompts scheduled by setting anchor 5 to the ADR hearing date. Ten days before the anchor 5 date (ADR hearing date), the program prompts an operator to determine the type of ADR (mediation or arbitration), and make appropriate entry into the corresponding client record. Next, the operator is prompted to generate a letter to the client confirming whether it is an arbitration or mediation in accordance with data entered in the client record in response to the type of ADR determined. Also at the ten day point, the program prompts the operator to determine whether the defendant is represented by insurance or alternatively by an attorney, and then prompts generation of a confirmation letter reflecting the appropriate ADR type to the appropriate representative of the defendant. Five days before the anchor 5 date, the program prompts the operator to check whether a statement has been filed with the mediator or arbitrator, and prompts the operator to generate and send the statement if not yet filed. Two days before the anchor 5 date, the program prompts telephone calls to the client, opposition, and mediator/arbitrator confirming the hearing.

If an ADR hearing has not been set, then conditional 128 is encountered. In conditional 128, a test is performed to determine if litigation has been initiated. If it has, then anchor 6 is set to the date the filed stamped complaint is returned. The scheduling of prompts for anchor 6 is detailed in scheduling routine 500 of FIG. 6. Routine 500 starts by timing 30 days from the return of the marked complaint (anchor 6 date) in block 502. At the 30 day point, the program prompts the operator to determine if an answer to the complaint, notice of service of the complaint on the defendant or defendant's representative, or a request for an enlargement of time to answer has been received in conditional 504. If service of the complaint is not verified, then the operator is prompted to re-serve the complaint in operation 506. If an answer is received, then preparation of informal (paper) discovery is prompted in operation 508.

Next, the program times a total of 60 days from the anchor 6 date in block 510. The program then re-prompts whether the answer, notice of service, or enlargement of time to answer in conditional 512. If service is not verified at the 60 day point, then re-service is prompted in operation 514. If an answer is received, then preparation of informal discovery is prompted in operation 516. If discovery has already been prepared in operation 508, then operation 516 may be ignored. The program then times a total lapse of 90 days from the anchor 6 date in operation 518 and prompts preparation and filing of a motion to set the trial date with the court. The program times 180 days from the anchor 6 date in operation 520 and executes a conditional to prompt the determination of whether a trial date has been set. If the trial date has not been set, operation 522 is encountered which prompts generation and filing of a second motion to set a trial date with the court. The prompts of schedule 500 are then completed.

Anchors 7–16 are also provided to facilitate the advancement and tracking for discovery performed by all parties to the lawsuit. Anchor 7 is set to the date a first set of informal discovery requests are sent to the defendant. Several prompts are conditionally provided by a program at various intervals relative to the anchor 7 date. These prompts follow-up on receipt of a response to the discovery sent on behalf of the client, and results in prompting a motion to be filed with the court to compel answers to the discovery if a response is not provided after following-up. Anchors 8 and 9 are directed to tracking second and third sets of informal discovery, respectively. Anchors 8 and 9 employ the same schedule of conditional prompts as anchor 7.

Anchors 10–12 are directed to various dates related to the arrangement and performance of a deposition on behalf of the client. Anchor 13 is set to the date informal discovery of the client (plaintiff) is received from the defendant. A series of prompts are scheduled relative to the anchor 13 date to assure a response is generated and sent to the defendant's representative. Anchors 14 is set to the date the deposition of the client by the defendant has actually been arranged. Anchor 14 prompts the generation of confirmation letters to the client and the defendant's attorney. Anchors 15 and 16 are directed to confirming the deposition just prior to the arranged date and to assure a copy of the transcript is received from the court reporter, reviewed by the client, and returned with comments as needed.

Anchor 17 is set to the date a trial for a client's case is set to be held. Anchor 17 is detailed in scheduling routine 600 of FIGS. 7A and 7B. Routine 600 starts by prompting the generation of dispositive motions 95 days before the trial start date (anchor 17 date) in operation 602. Block 604 signifies timing by the program to flag the point 90 days before the anchor 17 date. At the 90 day point, conditional 606 inquires into whether dispositive motions have been mailed. If not, mailing of the motions is prompted under operation 608. The program times 65 days prior to trial and prompts preparation of a preliminary witness and exhibit list for filing with the court under operation 610. Operation 610 also prompts filing of a list of contentions concerning the client's case which outline the client's position with respect to pertinent factual and legal issues. Operation 610 also prompts preparation and filing of motions in limine.

At 60 days before trial, as represented by block 612, conditional 614 prompts the determination of whether motions in limine have been filed. If motions in limine have not been filed, then mailing of the motions is prompted in operation 616. Next, operation 618 is encountered wherein completion of formal discovery is prompted. In addition, operation 618 prompts preparation and delivery of an affidavit to one or more medical providers to be executed and returned for presentation as evidence during trial. In block 620, time lapses until 35 days before trial when conditional 622 prompts to determine whether all outside information needed for trial has been received. If information is missing, completion of discovery is prompted in operation 624. At the 35 day point, operation 626 prompts the preparation of final witness and exhibit lists. After waiting until 30 days before trial, as represented by operation 628, conditional 630 prompts to determine whether the final witness and exhibit lists have been mailed. If the final lists have not been mailed, mailing of the final lists is prompted by operation 632. At 30 days before trial, the program also prompts the preparation and filing of proposed jury instructions under operation 634.

At 20 days before trial, the program prompts contacting the witness by letter under operation 636. Also, operation 636 prompts contacting medical providers by telephone from which affidavits have not been received. At 15 days before trial, as represented by block 638, conditional 640 tests whether any affidavits to medical providers still need to be mailed. If one or more affidavits do need to be mailed, then operation 642 prompts this mailing.

At 5 days before trial, the preparation of subpoenas and letters to witnesses is prompted. Also, conditional 646 prompts the determination of whether jury questionnaires have been received 5 days before the anchor 17 date. If not, operation 648 prompts contacting the clerk of the court to obtain the questionnaires. Routine 600 is then completed.

Collectively, each of anchors 1–18 initiates a sequence of conditional prompts which are scheduled to advance the client's case. In one embodiment, anchor 1 is initiated concurrently with anchor 2 upon creation of a new client record. Anchor 3 is initiated and clears anchor 2 once medical treatment is complete, removing any outstanding prompts of anchor 2. Similarly, sending a demand letter and correspondingly setting anchor 4 clears anchor 3 in this embodiment. On the other hand, Anchors 6–17 are permitted to operate concurrently given the nature of the litigation process.

Also, various other prompt schedules may be generated either separate from or in addition to various anchors. Generally, these independent schedules represent the operation of automated ticklers that are executed and tracked for a given client record by the management program independent of anchor dates or case phase. Furthermore, these independent prompts schedules may be set as often as needed for the same client and for multiple client records independent of one another. FIGS. 8A–8E illustrate several of the independent prompt schedules provided by the management program embodied in the computer program listing of the Microfiche Appendix.

Figure 8A:
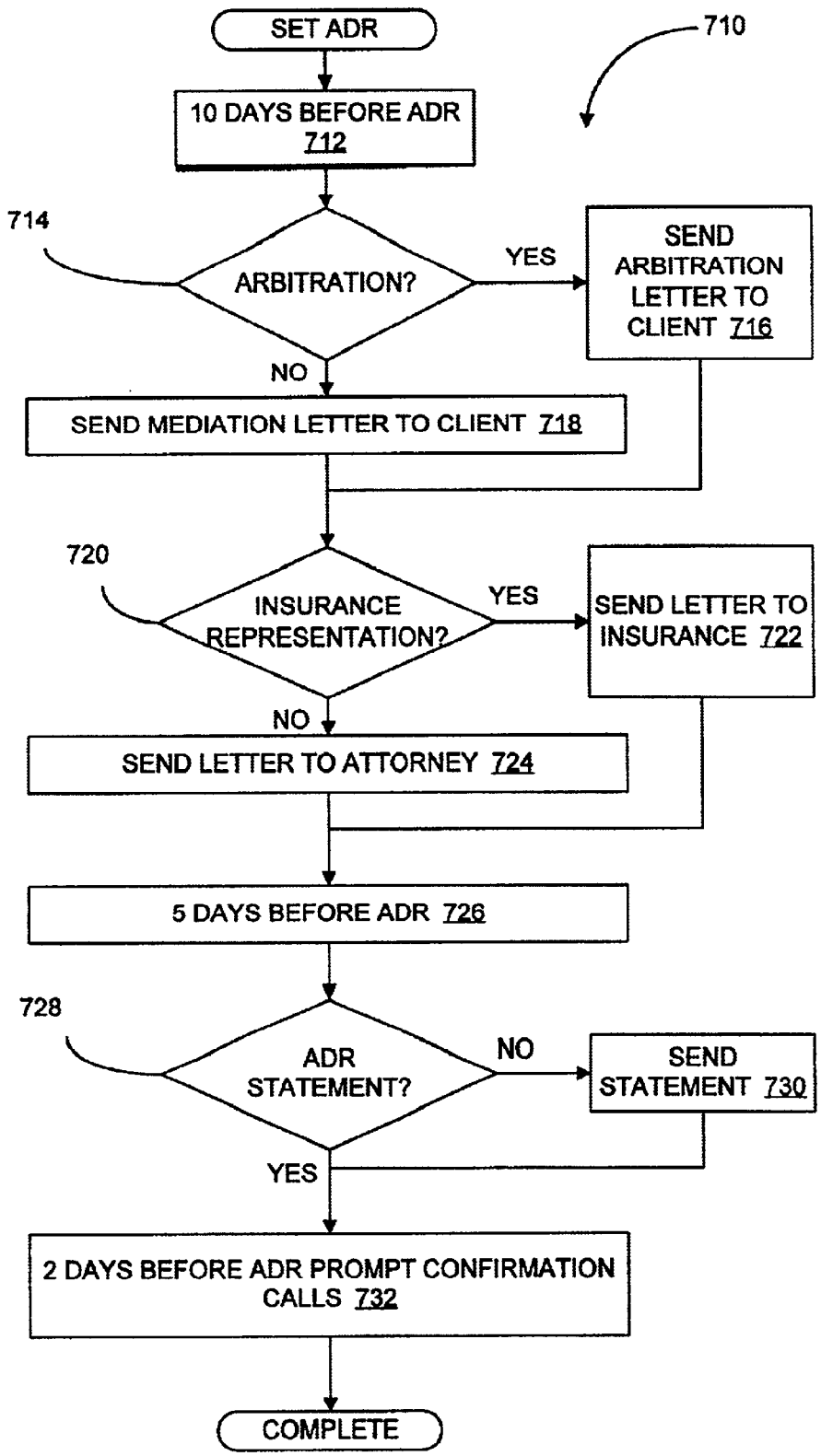
FIGS. 8A–8E are flow diagrams illustrating selected prompt scheduling routines to manage the process depicted in FIG. 2.

FIG. 8A is a flow diagram of schedule 710. Schedule 710 is initiated by starting a corresponding automated tickler with the ADR hearing date. Schedule 710 may be selected as an alternative to the anchor 5 schedule or otherwise employed throughout management of a client's case. Schedule 710 begins with block 712 which represents 10 days before the established ADR hearing date. At the 10 day point, conditional 714 determines whether the ADR is arbitration or mediation. If it is arbitration, operation 716 prompts preparation and delivery of an arbitration letter to the client. Otherwise, operation 718 prompts generation and delivery of a mediation letter to the client. Conditional 720 tests whether the defendant is represented by insurance or a personal attorney. If the defendant is represented by insurance, an ADR confirmation letter is prompted to the insurance attorney in operation 722. Otherwise, a letter to the defendant's personal attorney is prompted in operation 724.

Block 726 is next encountered which represents timing of 5 days before the ADR date. At this 5 day point, conditional 728 prompts whether an ADR statement has been filed with the mediator or arbitrator as appropriate. If the statement has not been filed, operation 730 prompts preparation and filing of the statement. In operation 732, the program prompts the attorney to place confirmation telephone calls to the appropriate parties. Schedule 710 is then completed.

Figure 8B:
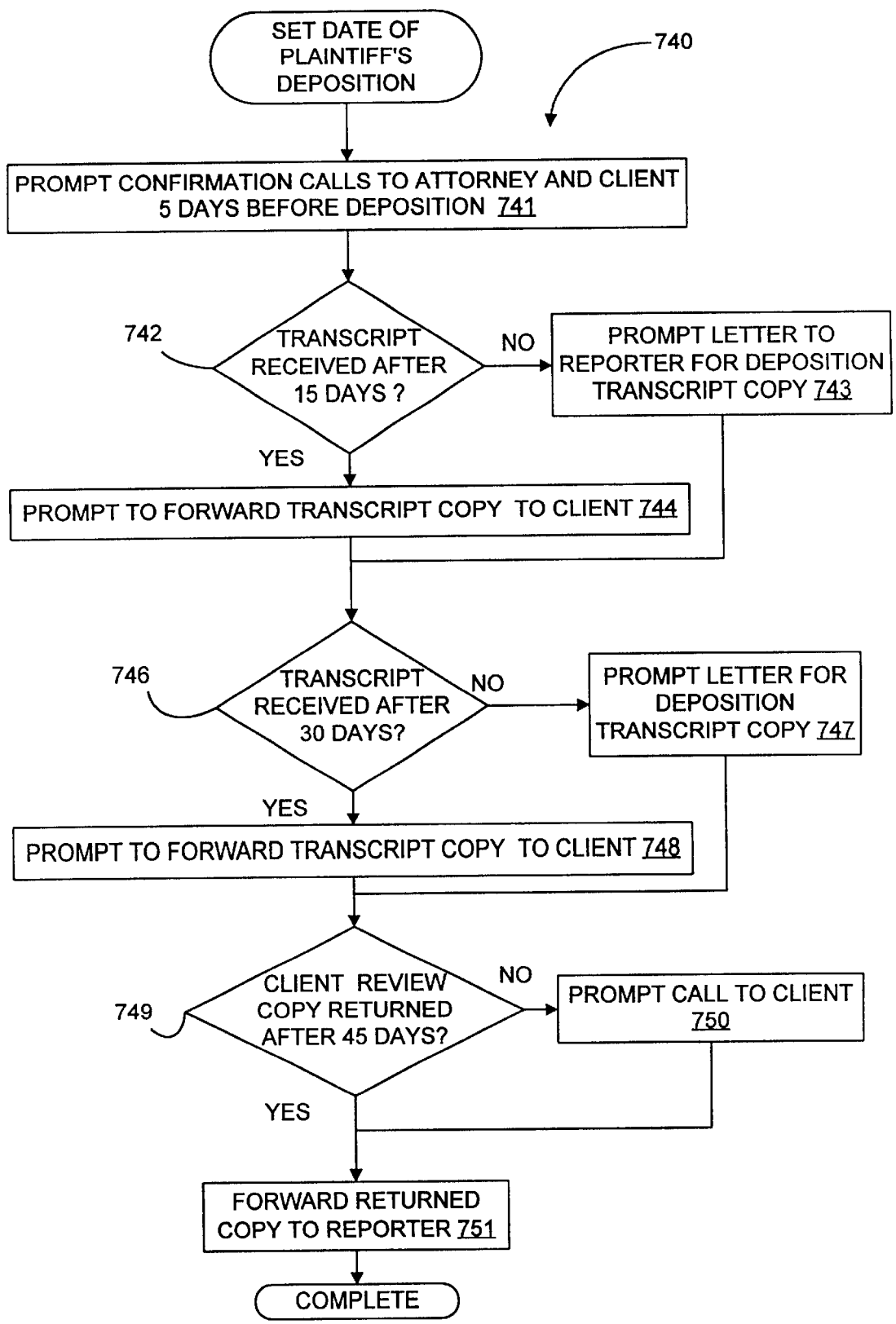

FIG. 8B is a flow diagram of prompt schedule 740 which may be set for each deposition of the client by the defendant. Schedule 740 is initiated by starting a corresponding automated tickler with the deposition date. Schedule 740 is configured to be set multiple times for each client. This schedule may be used in lieu of or in addition to anchors 14–16 associated with the stage 130 of the litigation phase. Schedule 740 starts in operation 741 by prompting confirmation calls to the client and opposing counsel 5 days before the deposition date. Control flows from operation 741 to conditional 742 to test whether a transcript for the deposition has been received 15 days after the deposition was taken. If the transcript was not received, operation 743 prompts generation of a letter to the reporter for the deposition transcript. Otherwise, the operator is prompted to forward the transcript to the client for review under operation 744. This review gives the client an opportunity to point out any inaccuracies or provide other comments as required. Next, conditional 746 is encountered which prompts whether the transcript has been received within 30 days following the deposition. If not, operation 747 prompts generation of a letter to the reporter requesting the transcript. Otherwise, the operator is prompted to forward a transcript copy to the client for review under operation 748 if the client has not yet received the transcript under operation 744. At 45 days after the deposition, conditional 749 tests whether the client has returned the transcript. If the copy has not been returned by the client, a telephone call to the client is prompted in operation 750. Otherwise, the transcript is forwarded to the court reporter in operation 751.

Figure 8C:
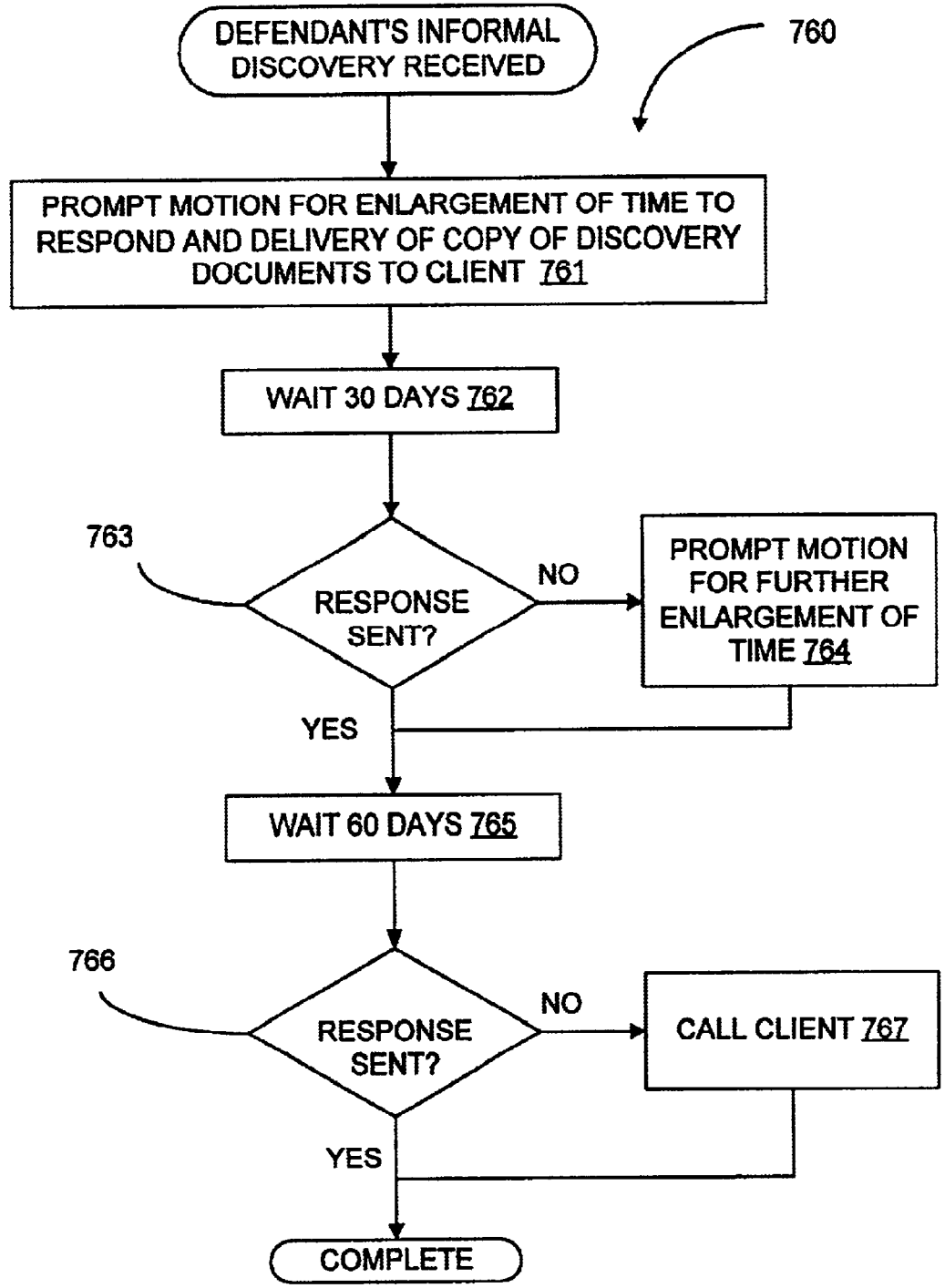

FIG. 8C is a flow diagram of prompt schedule 760 which is directed to tracking and responding to informal discovery served on the client by the defendant which may be in addition to or in lieu of anchor 13. Schedule 760 is initiated by setting a corresponding automated tickler to the date the defendant's informal discovery is received. Schedule 760 starts with operation 761 which prompts the preparation and filing of a motion for an enlargement of time to respond to the discovery.

Also, operation 761 prompts delivery of a copy of the discovery documents to the client. Block 762 represents the passage of 30 days form the date the discovery is received. At this 30 day point, conditional 763 is prompted which tests whether the discovery response has been sent. If the response has not been sent, then operation 764 prompts generation and filing of a second motion to enlarge the time to respond.

Block 765 is next encounter which times a total of 60 days from the service of the discovery. Conditional 766 prompts inquiry into whether the response has been sent at this 60 day point. If not, then operation 767 prompts a telephone call to the client. Schedule 760 is then regarded as complete.

Figure 8D:
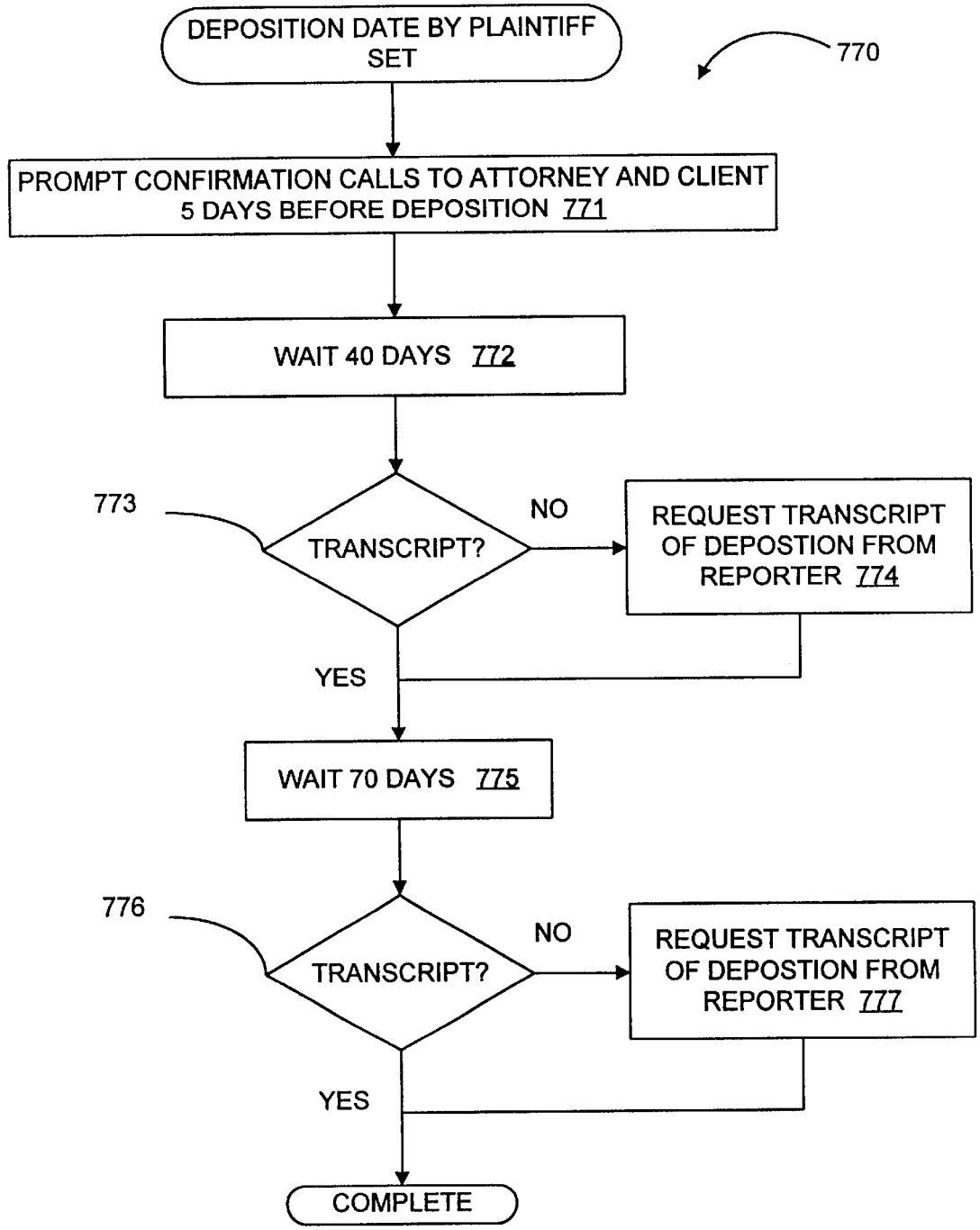

FIG. 8D is a flow diagram of prompt schedule 770 which is directed to tracking a deposition conducted by the plaintiff. Schedule 770 is initiated by setting a corresponding automated tickler to the deposition date. Schedule 770 may be used in addition to or in lieu of anchors 10–12. The program prompts confirmation calls to the client and opposing counsel 5 days before the scheduled deposition under operation 771. Block 772 times 40 days after the deposition date. At the 40 day point, conditional 773 prompts the determination of whether the deposition transcript has been received. If the transcript has not been received, then the transcript is requested from the reporter in operation 774. Next block 775 is encountered which times 70 days after the deposition. At the 70 day point, conditional 776 tests whether the transcript has yet been received. If the transcript has not been received, then operation 777 prompts a second request for original transcript from the reporter. At this point, schedule 770 is complete.

Figure 8E:
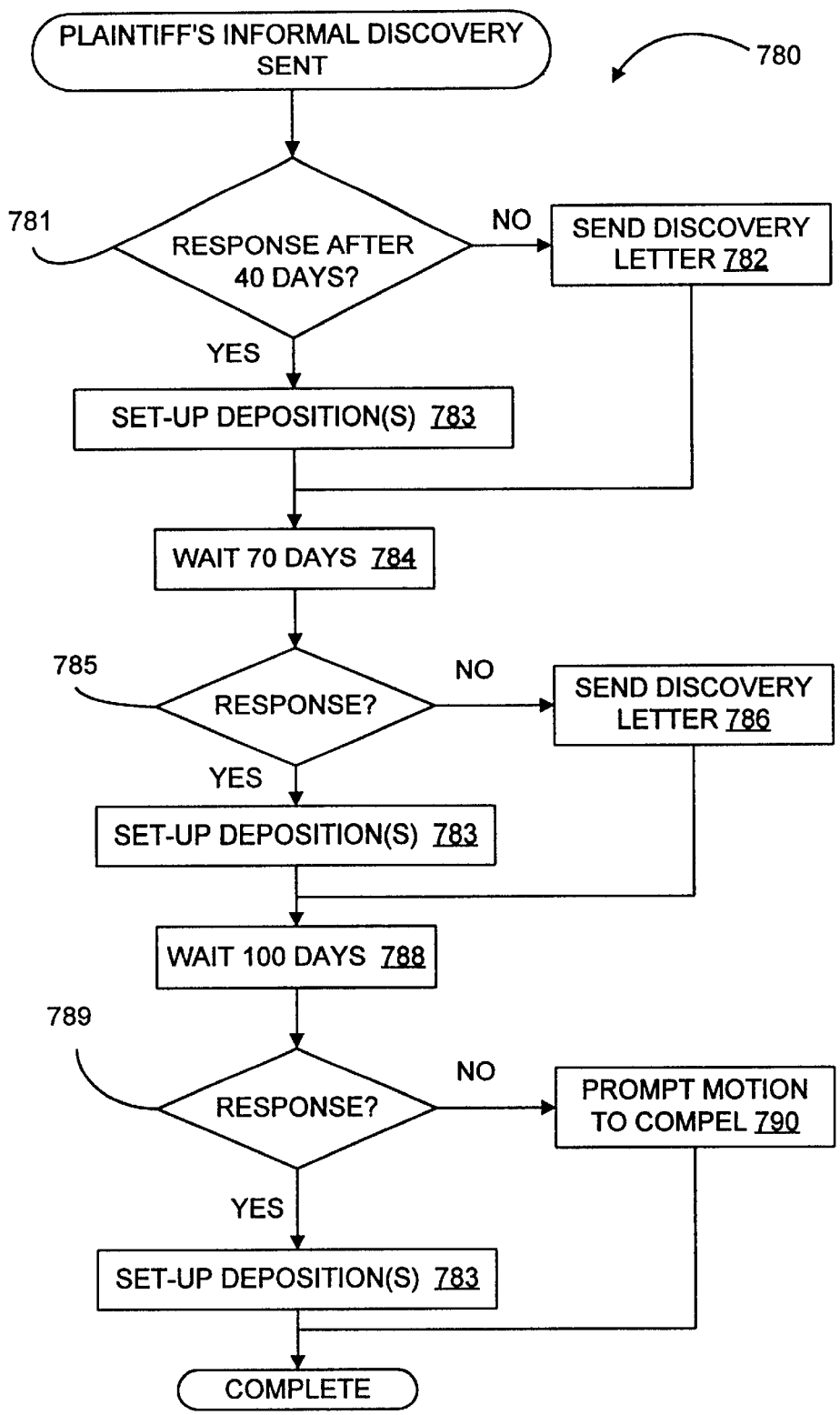

FIG. 8E is a flow diagram of prompt schedule 780 which is directed to tracking s progress of informal (paper) discovery served by the client (plaintiff) on others. Schedule 780 may be set one or more times for a given client to track informal discovery either in addition to or in lieu of anchors 7–9. Schedule 780 is initiated by setting a corresponding automated tickler to the date the discovery is served. Schedule 780 starts by timing 40 days from the date discovery is served and then executes conditional 781 to prompt an inquiry into whether a response was received from the recipient of the discovery. If the response has not been received, a request letter is sent to opposing counsel in operation 782. Otherwise, depositions on behalf of the client are set-up in operation 783. The deposition set-up may be accomplished by setting anchors 10–12 or initiating schedule 740 one or more times as required. Next, block 784 represents a time lapse of 70 days from the discovery service date. Conditional 785 is next encountered which again tests whether a discovery response has been received. If not, then a second discovery letter is prompted in operation 786. Otherwise depositions are initiated in operation 783. Block 788 then times a total lapse of 100 days. At the 100 day point, conditional 789 is encountered which tests again for a response. If a discovery response has still not been received, the operator is prompted to prepare and file a motion to compel discovery with the court under operation 790. Otherwise, depositions are arranged in operation 783 if not already done so. Schedule 780 is then complete.

In another feature of the present invention, follow-up prompts for various request letters generated by the management program may be generated by implementing automated ticklers in lieu of or in addition to prompts and ticklers of the various anchor schedules. In one embodiment, requests for medical records are generated with the management program during the pendency of anchor 2 for those medical providers whose treatment is already completed. When these requests are sent on behalf of clients, automated ticklers are set to automatically prompt a follow-up request letter or phone call after the passage of a predetermined amount of time. Notably, the medical record request operators of routine 200 for anchor 3 may still be used to request the records of the medical provider who treated the client up to the release of the client from medical treatment. Indeed, numerous automated ticklers of this type may be simultaneously set as needed for each client record independent of the anchor prompts.

As used herein, it should be appreciated that: "record," "form," "operation," "icon," "variable," "value," "buffer," "constant," "flag," "memory space," or "memory location" each generally correspond to a "signal" within processor 30 of the present invention. Furthermore it should be appreciated that as used herein: "variable," "value," "buffer," "constant," "flag," "threshold," "input," "output," "pixel," "image" (or a region thereof), "matrix," "command," or "memory location" each generally correspond to one or more signals within processing equipment of the present invention.

It is contemplated that various operations, records, icons, stages, conditionals, procedures, thresholds, blocks, forms, schedules, routines, and processes described in connection with the present invention could be altered, rearranged, substituted, deleted, duplicated, combined, or added to other processes as would occur to those skilled in the art without departing from the spirit of the present invention.

All publications, patents, and patent applications cited in this specification are herein incorporated by reference as if each individual publication, patent, or patent application were specifically and individually indicated to be incorporated by.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method, comprising:
   executing a program with a computer to manage a number of personal injury claims;
   establishing a number of client records corresponding to the claims with the program;
   generating a request for information with the program for a first one of the claims, the program automatically scheduling a computer prompt to an operator in response to said generating, the prompt being scheduled a period of time after said generating;
   providing the prompt to the operator after the period of time passes;
   receiving the information in response to the prompt;
   entering data into a first one of the records corresponding to the information; and
   wherein each of the records includes an indication of claim status and further comprising:
   setting the indication for the first one of the records to represent a pre-negotiation phase of the first one of the claims;
   sending a number of letters requesting medical treatment data in response to a number of operator prompts generated by the program during the pre-negotiation phase;
   entering the medical treatment data into the first one of the records in response to said sending;
   providing a communication to demand compensation for the personal injury after medical treatment is completed; and
   changing the indication for the first one of the records to represent a negotiation phase of the first one of the claims.

2. The method of claim 1, wherein the request includes a letter and further comprising performing said generating in response to a tickler to create the letter.

3. The method of claim 1, wherein the computer prompt is one of a sequence of prompts automatically scheduled by the program in response to generation of the request.

4. The method of claim 1, further comprising switching the indication to a litigation phase after said changing.

5. The method of claim 1, further comprising switching the indication to a settlement phase after said changing.

6. The method of claim 5, wherein a settlement check with an amount payable to a client for the first one of the claims is generated by the program during the settlement phase, the program automatically calculating the amount from expense information entered in the first one of the records.

7. The method of claim 1, wherein the pre-negotiation phase includes a first subordinate stage and a second subordinate stage, the program generating a first set of ticklers during the first subordinate stage and a second set of ticklers during the second subordinate stage, the operator prompts belonging to the second set of ticklers.

8. A method, comprising:
   executing a program with a computer to manage a number of personal injury claims;
   establishing a number of client records corresponding to the claims with the program;
   generating a request for information with the program for a first one of the claims, the program automatically scheduling a computer prompt to an operator in response to said generating, the prompt being scheduled a period of time after said generating;
   providing the prompt to the operator after the period of time passes;
   receiving the information in response to the prompt;
   entering data into a first one of the records corresponding to the information;
   prompting generation of a letter with the program to request medical data about a second one of the claims;
   automatically scheduling a follow up prompt with the program in response to said prompting; and
   entering the medical data into a second one of the records.

9. A method, comprising:
   executing a program with a computer to manage a number of personal injury claims;
   establishing a number of client records corresponding to the claims with the program;
   prompting requests for a group of documents each from a different source, the documents corresponding to a first one of the claims;
   scheduling a number of sequences of follow up prompts with the program, the sequences each corresponding to a different one of the documents and overlapping in time;
   receiving a first one of the documents;
   entering data into a first one of the records in response to receipt of the first one of the documents, the first one of the records corresponding to the first one of the claims;
   removing any of the follow up prompts scheduled for a first one of the sequences corresponding to the first one of the documents with the program in response to said entering;
   prompting generation of a letter with the program to request medical data about a second one of the claims;
   automatically scheduling a follow up prompt with the program in response to said prompting; and entering the medical data into a second one of the records.

10. The method of claim 9, further comprising:

receiving a second one of the documents after said removing;

updating the first one of the records with data corresponding to the second one of the documents after said receiving; and canceling any of the follow up prompts scheduled for a second one of the sequences corresponding to the second one of the documents with the program in response to said updating.

11. The method of claim 9, further comprising:

prompting requests for a number of document responses each corresponding to a second one of the claims;

scheduling a number of series of operator prompts with the program, the series each corresponding to a different one of the document responses;

receiving a first one of the document responses;

updating a second one of the records in response to receipt of the first one of the document responses, the second one of the records corresponding to the second one of the claims; and removing any of the operator prompts scheduled for a first one of the series corresponding to the first one of the document responses with the program after said updating.

12. The method of claim 9, wherein each of the records includes an indication of claim status, and further comprising:

setting the indication for the first one of the records to represent a pre-negotiation phase of the first one of the claims;

entering medical treatment data into the first one of the records during the pre-negotiation phase;

sending a communication to demand compensation for the personal injury after medical treatment is completed; and changing the indication for the first one of the records to represent a negotiation phase of the first one of the claims.

13. The method of claim 12, further comprising switching the indication to a litigation phase after said changing.

14. The method of claim 12, further comprising switching the indication to a settlement phase after said changing.

15. The method of claim 14, wherein a settlement check with an amount payable to a client for the first one of the claims is generated by the program during the settlement phase, the program automatically calculating the amount from expense information entered in the first one of the records.

16. The method of claim 12, wherein the pre-negotiation phase includes a first subordinate stage and a second subordinate stage, the program generating a first set of operator prompts during the first subordinate stage and a second set of operator prompts during the second subordinate stage.

17. A method, comprising:

executing a program with a computer to manage a number of plaintiff's personal injury claims;

establishing a number of client records with the program, the records corresponding to the claims and each including a indication corresponding to claim status;

setting the indication of a first one of the records to correspond to a pre-negotiation phase of a first one of the claims;

generating a number of computer prompts with the program, the prompts each corresponding to a different one of a number of requests for information during the pre-negotiation phase;

receiving the information for each of the requests in response to said generating;

entering data in the first one of the records corresponding to the information for each of the requests;

providing a tickler to an operator with the program in response to fulfillment of the requests to prompt action to advance the first one of the claims towards a negotiation phase;

prompting generation of a letter with the program to request medical data about a second one of the claims;

automatically scheduling a follow up prompt with the program in response to said prompting; and entering the medical data into a second one of the records.

18. The method of claim 17, wherein the pre-negotiation phase includes a first subordinate stage and a second subordinate stage, the program generating a first set of operator prompts during the first subordinate stage and a second set of operator prompts during the second subordinate stage, the second set of operator prompts including the number of computer prompts.

19. The method of claim 17, further comprising:

making a respective one of the requests with a document generated in response to a corresponding one of the computer prompts; and automatically scheduling a follow up prompt in response to said making with the program, the prompt being scheduled a predetermined time after said generating.

20. The method of claim 17, further comprising sending a communication to demand compensation for the personal injury in response to the tickler.

21. The method of claim 20, further comprising:

generating the communication with the program in response to the tickler before said sending, the program including a sequence of stages to facilitate formation of the communication with the computer; and changing the indication for the first one of the records to represent the negotiation phase.

22. The method of claim 20, further comprising switching the indication to a litigation phase after said sending.

23. The method of claim 20, further comprising switching the indication to a settlement phase after said sending.

24. The method of claim 17, further comprising scheduling a number of sequences of follow up prompts with the program, the sequences each corresponding to a different one of the requests.

* * * * *